US010520478B2

(12) United States Patent
Pierce

(10) Patent No.: US 10,520,478 B2
(45) Date of Patent: *Dec. 31, 2019

(54) FLUIDLESS COLUMN OVEN FOR GAS CHROMATOGRAPHY SYSTEM

(71) Applicant: GC OVENS INC., Henderson, NV (US)

(72) Inventor: David R. Pierce, Bad Honnef (DE)

(73) Assignee: GC OVENS INC., Henderson, NV (US)

( * ) Notice: Subject to any disclaimer, the term of this patent is extended or adjusted under 35 U.S.C. 154(b) by 93 days.

This patent is subject to a terminal disclaimer.

(21) Appl. No.: 15/894,699

(22) Filed: Feb. 12, 2018

(65) Prior Publication Data

US 2018/0348173 A1   Dec. 6, 2018

Related U.S. Application Data

(63) Continuation of application No. 15/727,006, filed on Oct. 6, 2017, now Pat. No. 9,927,406.

(Continued)

(51) Int. Cl.
*G01N 30/30* (2006.01)
*G01N 30/02* (2006.01)
*G01N 30/72* (2006.01)

(52) U.S. Cl.
CPC ......... *G01N 30/30* (2013.01); *G01N 30/7206* (2013.01); *G01N 2030/025* (2013.01); *G01N 2030/3015* (2013.01); *G01N 2030/3038* (2013.01); *G01N 2030/3046* (2013.01); *G01N 2030/3053* (2013.01);

(Continued)

(58) Field of Classification Search
CPC ........... G01N 30/30; G01N 2030/3015; G01N 2030/3038; G01N 2030/3046; G01N 2030/3053; G01N 2030/3061; G01N 2030/3069; G01N 2030/3076; G01N 2030/3084

See application file for complete search history.

(56) References Cited

U.S. PATENT DOCUMENTS 3,053,077 A   9/1962   Tracht
3,146,616 A   9/1964   Loyd
(Continued)

FOREIGN PATENT DOCUMENTS

FR         2062110        6/1971
WO    WO 2015/144117     10/2015

OTHER PUBLICATIONS

Search Report issued in United Kingdom App. No. GB1809085 (dated Dec. 3, 2018).

(Continued)

*Primary Examiner* — Robert Clemente
(74) *Attorney, Agent, or Firm* — Barnes & Thornburg LLP

(57) ABSTRACT

A system for performing gas chromatography analyses in accordance with the present disclosure includes an analytical column and a column oven. The analytical column has an inlet portion coupled to an injector for receiving a material sample and an outlet portion coupled to a detector. The analytical column is adapted to direct the material sample from the injector to the detector. The column oven is adapted to heat the analytical column for separating constituent components of the material sample for detection by the detector.

18 Claims, 14 Drawing Sheets

Related U.S. Application Data

(60) Provisional application No. 62/514,527, filed on Jun. 2, 2017.

(52) U.S. Cl.
CPC ............... *G01N 2030/3061* (2013.01); *G01N 2030/3076* (2013.01); *G01N 2030/3084* (2013.01)

(56) References Cited

U.S. PATENT DOCUMENTS

| | | | |
|---|---|---|---|
| 4,181,613 | A | 1/1980 | Welsh et al. |
| 4,923,486 | A | 5/1990 | Rubey |
| 5,028,243 | A | 7/1991 | Rubey |
| 5,114,439 | A | 5/1992 | Yost et al. |
| 5,215,556 | A | 6/1993 | Hiller et al. |
| 5,808,178 | A | 9/1998 | Rounbehler et al. |
| 6,427,522 | B1 | 8/2002 | Thomas et al. |
| 7,104,112 | B2 | 9/2006 | Bonne |
| 7,228,067 | B2 | 6/2007 | Magni et al. |
| 9,194,849 | B2 | 11/2015 | Kanai et al. |
| 9,927,406 | B1 * | 3/2018 | Pierce .................... G01N 30/30 |
| 2009/0320560 | A1 | 12/2009 | Ross |
| 2012/0318782 | A1 | 12/2012 | Collins et al. |
| 2016/0266076 | A1 | 9/2016 | Fogwill et al. |

OTHER PUBLICATIONS

*DPS Instruments, Inc. Introduces "Companion" Gas Chromatograph* (Feb. 20, 2008).
*DPS Instruments, Inc. Introduces "Companion" Portable Gas Chromatograph's* (Dec. 2, 2008).
*DPS Instruments, Inc. Introduces "Companion" Portable Gas Chromatograph's* (Sep. 21, 2010).
*DPS Companion 2 GC* Brochure (Sep. 2010).
*DPS Companion 2 GC* Brochure (Jan. 2016).
Hinshaw, John V., *Gas Chromatography Ovens*, LCGC Asia Pacific, vol. 18, No. 1, pp. 17-21 (Mar. 1, 2015).

\* cited by examiner

FLUIDLESS COLUMN OVEN FOR GAS CHROMATOGRAPHY SYSTEM

CROSS REFERENCE TO RELATED APPLICATIONS

This application is a continuation of co-pending U.S. patent application Ser. No. 15/727,006, filed Oct. 6, 2017, which claims the benefit of priority under 35 U.S.C. § 119(e) to U.S. Provisional Patent Application No. 62/514,527, filed Jun. 2, 2017. The disclosures set forth in the referenced applications are incorporated herein by reference in their entireties.

FIELD OF THE DISCLOSURE

The present disclosure relates generally to gas chromatography ("GC") or gas chromatography mass spectrometry ("GCMS") analyses, and more specifically to GC systems used to conduct GC analyses.

BACKGROUND

At a basic level, a GC system contains an injector, an analytical column, a column oven, and a detector. A sample of material to be analyzed enters the analytical column through the injector along with a carrier gas for carrying compounds to the detection device. The analytical column is positioned inside a temperature controlled column oven and separates the constituent compounds of the material sample for detection by the detector. The column oven can be held at a constant isothermal temperature, or can be programmed to increase temperature over time, to separate and elute the constituent compounds of the material sample. Once released from the column, the carrier gas sweeps the compounds to the detector. Each measured compound in the material sample is represented as a peak on an output chart. The retention time of each compound, as shown by the peaks, is used by the GC system to identify the chemical makeup of the material sample. An example of an isothermal column oven with a direct heating column assembly is described in, for example, U.S. Pat. No. 7,228,067. An example of temperature programmed oven for moving a temperature gradient along a analytical column is described in, for example, U.S. Pat. No. 3,146,616.

Previous column ovens use a fluid (e.g., water, oil, air, or other liquid or gas) for temperature control of the thermal environment surrounding the analytical column. See, e.g., John V. Hinshaw, "Gas Chromatography Ovens", *LCGC Asia Pacific*, Vol. 18, No. 1, pp. 17-21. At least one disadvantage of a liquid fluid was keeping the fluid from ruining the analytical column when changing the column, or from leaks through loose fittings. Air bath ovens also suffer from extended lag times in reaching a set-point temperature and added cooling requirements such as the systems shown in, for example, U.S. Pat. Nos. 3,053,077 and 4,181,613.

Once an isothermal oven has equilibrated from initial start-up, maintaining temperature is relatively easy because the oven temperature never changes between analysis runs. However, only compounds with similar boiling points can be separated at a single temperature. For the analysis of a broader range of compounds a temperature program is generally used. When a temperature program is initiated, there is a slight lag time between the column temperature and the set-point temperature of the ramp. As the temperature increases the actual oven temperature lags behind the set-point and the column lags more. This temperature lag is greater at higher ramp rates, because it takes longer for the heat to transfer from the oven element, through the air fluid, to the column. The GC system must be capable of repeating the same time and temperature profile from run to run. Choosing narrower and shorter columns for fast GC greatly increases the demands on the column oven. Additionally, temperature programmed ovens require a cooldown and equilibration time between runs. Common practice is to let air bath ovens equilibrate for an extra 2-4 min after the set-point has been reached, to allow this residual heat to dissipate.

Additional advances in temperature control circuits and turbulent mixing of air over the past few decades have resulted in modern GC designs permitting precise GC oven temperature control, although they still suffer from the setbacks described above with respect to equilibration time, residual heat, the stability of the environmental air, temperature lag, and the requirement of precise consistency from run to run.

While gas chromatography is a powerful tool for separating complex mixtures into individual components for identification and quantification, the GC analysis generally requires long analysis times, typically in the 30-60 minute range. Advances in fast GC analyses initially involved faster temperature ramping and faster oven cooling between analyses, using higher power heating elements and more powerful cooling fans. See, e.g., U.S. Pat. Nos. 4,923,486, 5,028,243, 5,215,556, 5,808,178, 5,114,439, 6,427,522, 9,194,849, and WO Pub. No. 2015/0144117. These have proved successful in reducing the heating and cooling cycle times to some degree. However, providing faster analyses in a traditional fluid oven requires compromises. Speeding up the GC temperature program alone can result in reduced column separation efficiency and reduced column lifetime. These systems also do not work with varying column types and/or lengths and still require fluid for controlling temperature.

Each of these fluid oven attempts at reducing the GC analysis times has limitations. Most GC methods are intended to detect compounds at the lowest possible levels, which implies that one needs to introduce as much material sample as possible into the analytical column for separation and detection. Short, narrow bore columns are not suited for low level compound analyses. Faster heating and cooling helps with longer analytical columns, but the column still needs come to temperature equilibrium before the next material sample is injected for the results to be reproducible, adding a few extra minutes to each cycle.

SUMMARY

According to one aspect of the present disclosure, a system for performing gas chromatography analyses includes an analytical column and a column oven. The analytical column has an inlet portion coupled to an injector for receiving a material sample and an outlet portion coupled to a detector. The analytical column is adapted to direct the material sample from the injector to the detector. The column oven is adapted to heat the analytical column for separating constituent components of the material sample for detection by the detector.

In illustrative embodiments, an inlet heater is coupled to the inlet portion of the analytical column and configured to produce one or more heat zones along the inlet portion of the analytical column. An outlet heater is coupled to the outlet portion of the analytical column and configured to produce one or more heat zones along the outlet portion of the analytical column. A controller is operatively coupled to the inlet heater and the outlet heater, and selectively powers the inlet heater and the outlet heater to define a steady-state temperature profile along the analytical column.

In illustrative embodiments, the inlet heater is configured to produce at least a first heat zone and second heat zone. The first heat zone is generated by a first section of resistive heating wire having a first diameter, the second heat zone is generated by a second section of resistive heating wire coupled to an end of the first section of resistive heating wire, and the second section of resistive heating wire has a second diameter different than the first diameter. The outlet heater is configured to produce at least a third heat zone and fourth heat zone. The third heat zone is generated by a third section of resistive heating wire having a third diameter, the fourth heat zone is generated by a fourth section of resistive heating wire coupled to an end of the third section of resistive heating wire, and the fourth section of resistive heating wire has a fourth diameter different than the third diameter.

In illustrative embodiments, the temperature profile has at least a first temperature gradient and a second temperature gradient. The first temperature gradient is negative and the second temperature gradient is positive.

In illustrative embodiments, the inlet heater is configured to produce at least a first heat zone along the inlet portion of the analytical column, and the outlet heater is configured to produce at least a second heat zone along the outlet portion of the analytical column. The first heat zone is maintained by the controller at a first temperature and the second heat zone is maintained by the controller at a second temperature. The second temperature is less than the first temperature.

In illustrative embodiments, at least one of the inlet heater and the outlet heater is configured to produce a third heat zone positioned between the first and second heat zones along the analytical column. The third heat zone is maintained by the controller at a third temperature. The third temperature is less than both the first and second temperatures.

In illustrative embodiments, the inlet heater and outlet heater are part of a fluidless column oven. The inlet heater is coupled to a first portion of a support frame of the fluidless column oven. The outlet heater is coupled to a second portion of the support frame different than the first portion.

According to another aspect of the present disclosure, a method for performing fast gas chromatography includes creating a first steady-state temperature gradient along an inlet portion of an analytical column using an inlet heater, creating a second steady-state temperature gradient along an outlet portion of the analytical column using an outlet heater, and passing a sample of material to be analyzed from an injector through the analytical column to a detector such that constituent compounds of the sample separate and elute for detection by the detector.

In illustrative embodiments, the first and second temperature gradients are different. The inlet heater is configured to form at least two heat zones along the inlet portion of the analytical column, and each heat zone has a different temperature. The outlet heater is configured to form at least two heat zones along the outlet portion of the analytical column, and each heat zone has a different temperature.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The detailed description makes reference to the accompanying figures in which.

DETAILED DESCRIPTION

Figure 1:
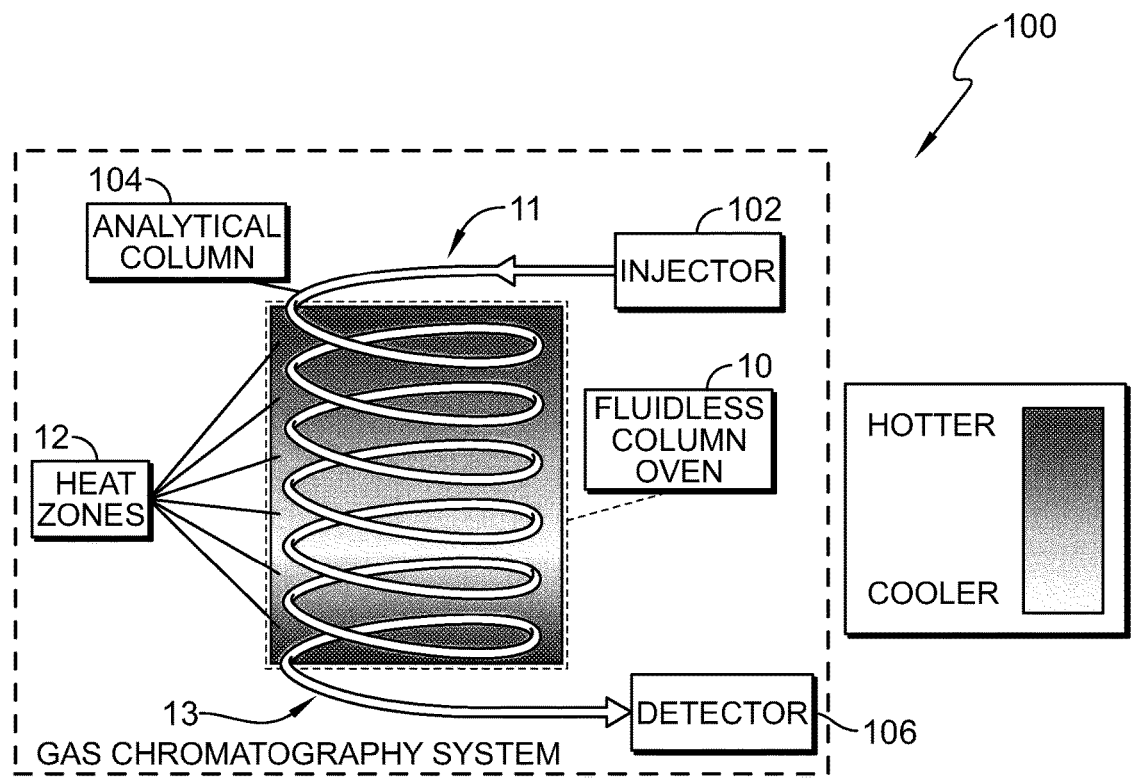
FIG. 1 is a diagrammatic view of a gas chromatography (GC) system in accordance with the present disclosure showing that the GC system includes an injector coupled to an analytical column for sending a sample of material to be analyzed toward a detector and suggesting that a fluidless column oven of the GC system forms a plurality of heat zones along the column to define a temperature profile as suggested in FIG. 2.

A gas chromatography ("GC") system 100 in accordance with the present disclosure is shown in FIG. 1. Gas chromatography system 100 includes an injector 102 coupled to an analytical column 104 for sending a sample of material to be analyzed toward a detector 106. A fluidless column oven ("FCO") 10 of GC system 100 forms a plurality of heat zones 12 to define a steady-state temperature profile along analytical column 104 as suggested in FIGS. 1 and 2. As used herein, the term "fluidless" in relation to column oven 10 means no fluid (e.g., water, oil, air or other liquid or gas) is used to heat or cool analytical column 104 to maintain the column temperature. In other words, a fluid is not the main driver of temperature control in FCO 10 according to the present disclosure as is further explained in detail herein. Analytical column 104 includes an inlet portion 11 coupled to injector 102 and an outlet portion 13 coupled to detector 106 as shown in FIG. 1.

Figure 2:
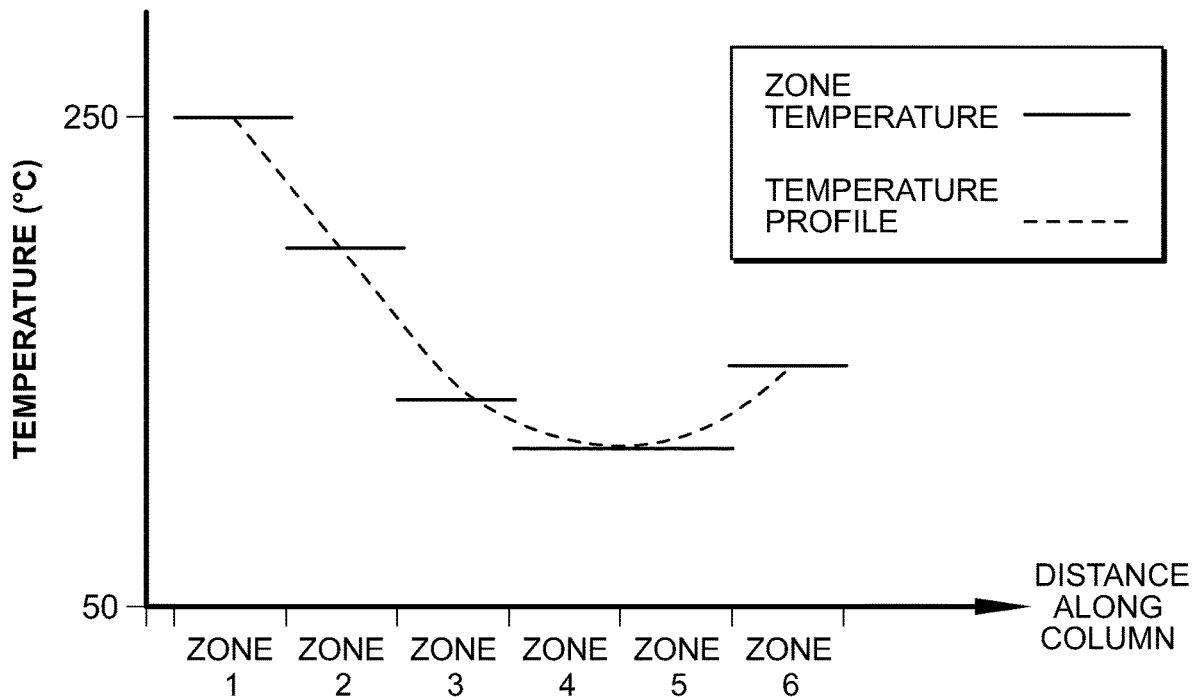
FIG. 2 is a graph showing one embodiment of a temperature profile in accordance with the present disclosure defined by the varying temperatures in the heat zones of the GC system of FIG. 1.

One embodiment of a temperature profile defined by FCO 10 in accordance with the present disclosure is shown in FIG. 2. In the illustrative embodiment, FCO 10 is configured to form six heat zones positioned along analytical column 104 with zones 1-3 positioned along inlet portion 11 and zones 4-6 positioned along outlet portion 13. Each of heat zones 1-6 can be adjusted to have the same or different temperatures compared to an adjacent heat zone. Each heat zone is directly adjacent to the next heat zone and share heat between them to form a smooth continuous temperature curve. The temperature profile, as defined by the heat zones of FCO 10, includes a negative temperature gradient portion, such as along inlet portion 11, and a subsequent positive temperature gradient portion, such as along outlet portion 13, based on varying temperatures between the heat zones 1-6. As used herein, the term "temperature profile" generally refers to the temperatures experienced along a length of the analytical column. As used herein, the term "temperature gradient" generally refers to a positive or negative change in the temperature profile. In some embodiments, the temperature profile includes a positive temperature gradient portion and subsequent negative temperature gradient portion. In some embodiments, the temperature profile has an overall negative temperature gradient or an overall positive temperature gradient. In some embodiments, the temperature profile has a temperature gradient of substantially zero.

In GC analyses, the relationship between column temperature and compound retention is fundamental. Retention times are controlled by managing column temperature and the column pressure drop influenced by the carrier gas. A stable column oven temperature environment is essential to maintain consistent retention times for compounds eluting from the analytical column. A slight change in oven temperature can cause significant retention time shifts affecting the proper identification of compounds in a sample of material being analyzed. Slightly higher overall oven temperatures cause compounds to be eluted earlier, with a reduced retention time, while a slightly lower oven temperature will cause compounds to elute later, with an increased retention time. In addition to run-to-run temperature changes, variables such as spatial fluctuations along the column, caused by temperature gradients and dynamic short-term oven temperature fluctuations, also contribute to the problem of retention time shifts. For the fastest analysis cycle, it is best to eliminate the heating and cooling cycle and maintain the column at equilibrium.

Generally, lower boiling compounds travel through the negative gradient at a faster rate than higher boiling compounds of the material sample. The interaction of compounds with the stationary phase inside analytical column 104 plays the same role in compound separation as it would in a conventional air bath oven. Consequently, the chromatograms produced with FCO 10 (such as those shown in FIGS. 7 and 8) have the same compound elution sequence as they would with an air bath oven. As an extra benefit, the negative temperature gradient focuses the peaks because the front of the peak is at a slightly lower temperature than the back of the peak, which serves to slow the front with respect to the back, and sharpens and focuses the peaks as they travel down the negative gradient. The subsequent positive gradient increases pressure at outlet portion 13 to further slightly compress the peaks.

Figure 3:
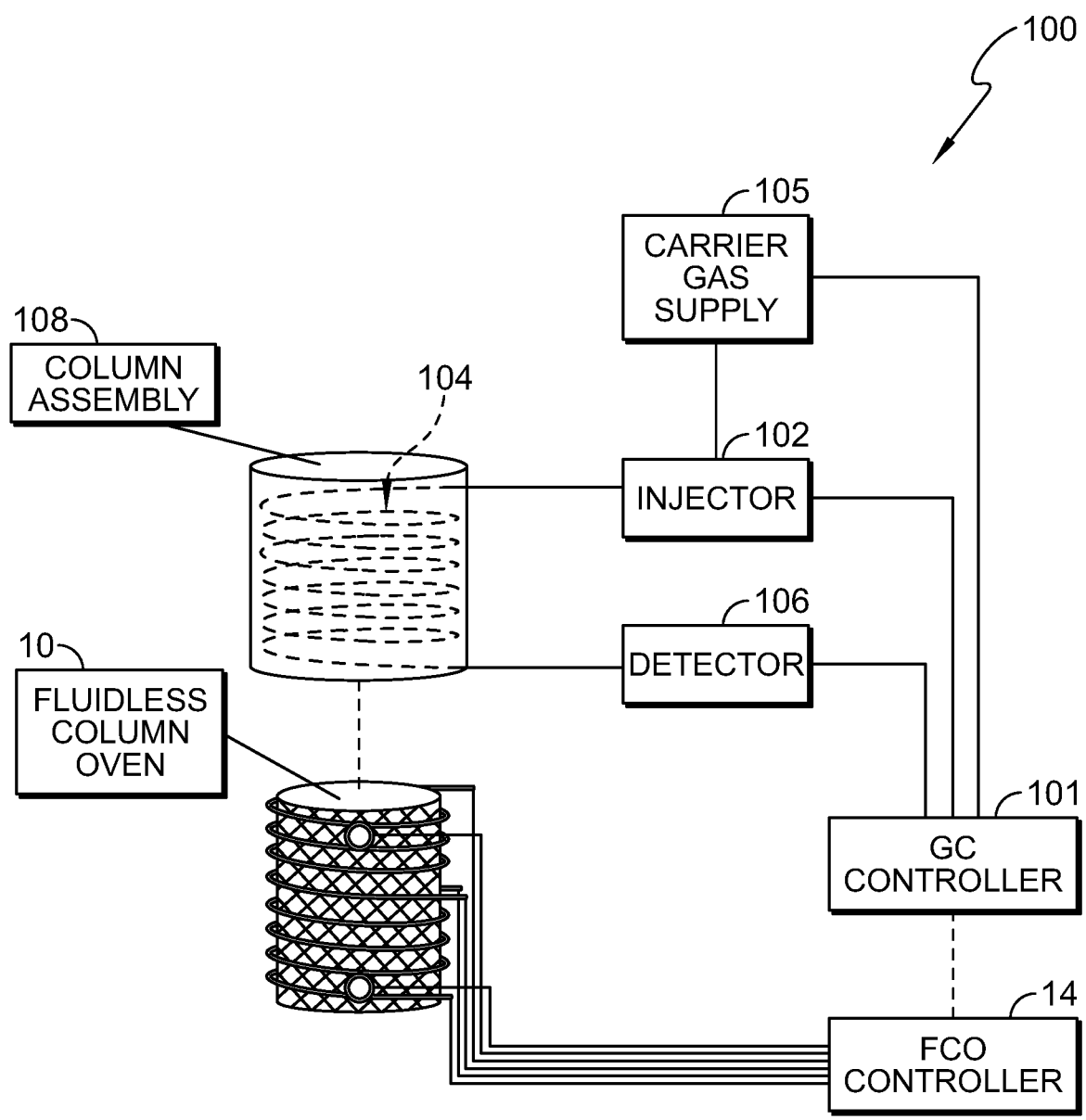
FIG. 3 is an exploded assembly view of the GC system of FIG. 1 showing the fluidless column oven separated from a column assembly of the GC system and suggesting that the fluidless column oven is received in the column assembly for heating the analytical column in the column assembly.
Figure 7:
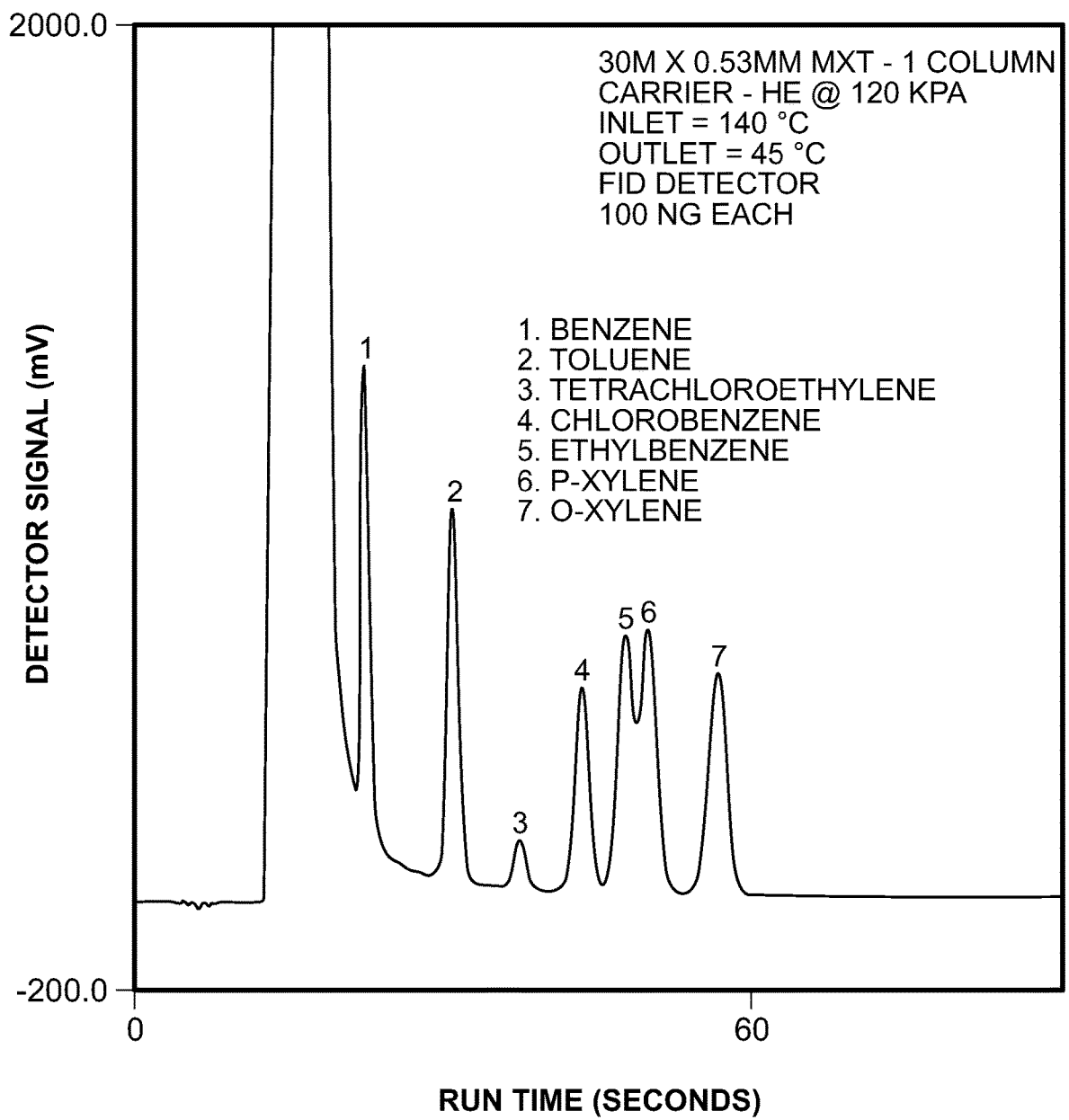
FIG. 7 is a chromatogram of a BTEX (benzene, toluene, ethylbenzene, and xylenes) analysis using a GC system in accordance with the present disclosure.
Figure 8:
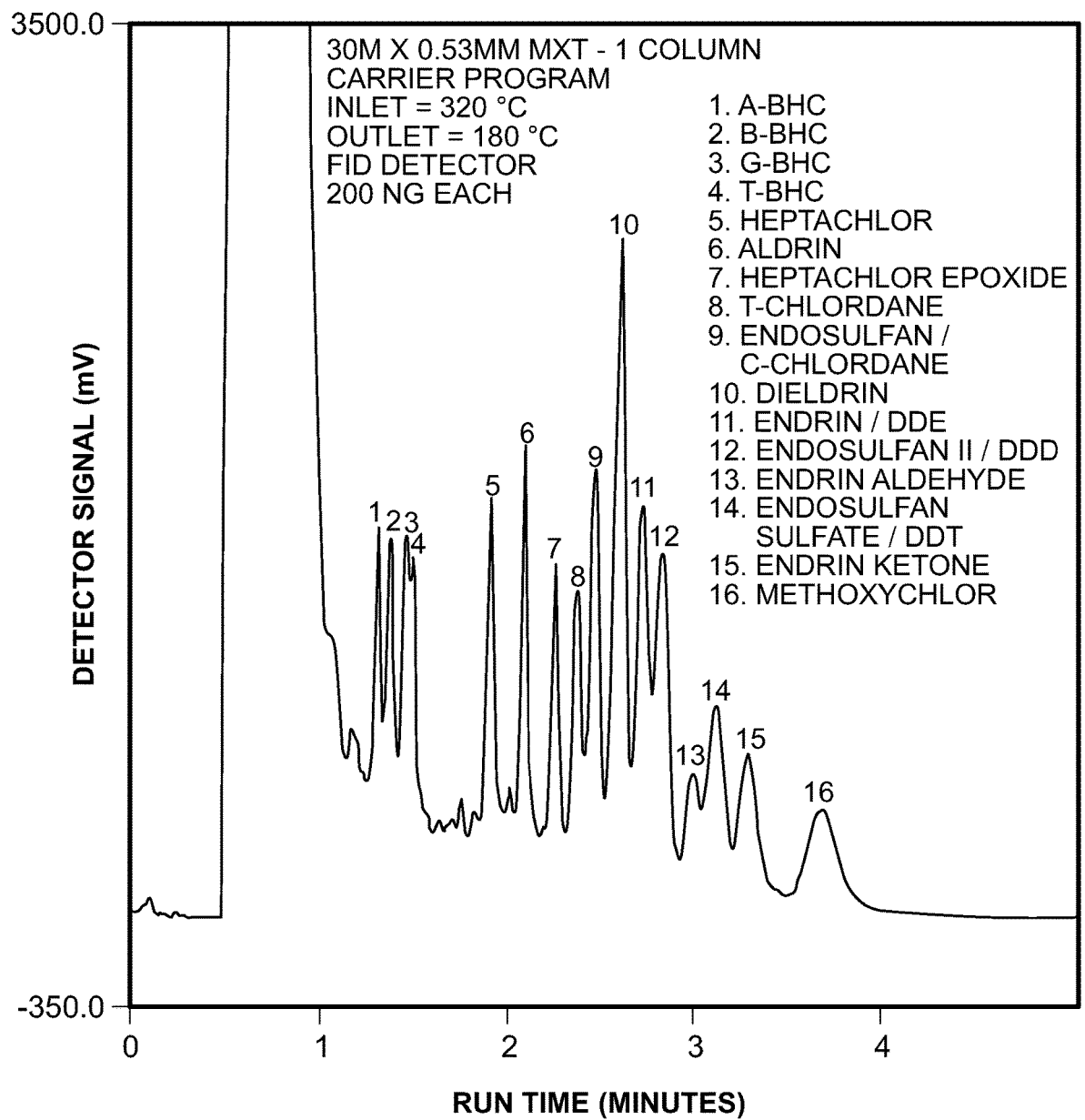
FIG. 8 is a chromatogram of a organochlorine pesticide analysis using a GC system in accordance with the present disclosure.

Fluidless column oven 10 is configured to be received in a column assembly 108 of GC system 100 as suggested in FIG. 3. Different column assemblies 108 can be used with FCO 10 such as, for example, column assemblies 108 having varying types and lengths of analytical columns 104. FCO 10 can also be used with varying GC systems 100. In the illustrative embodiment, FCO 10 is coupled to a FCO controller 14 for adjusting and maintaining the temperature profile formed by FCO 10. A carrier gas supply 105 provides a carrier gas for moving a sample of material being analyzed by GC system 100 through injector 102 and analytical column 104 toward detector 106. A GC controller 101 is independent of FCO controller 14 and controls operations of GC system 100, such as parameters of carrier gas supply 105, injector 102, and detector 106. In some embodiments, GC Controller 101 is able to perform the functions of FCO Controller 14 such that a stand-alone FCO controller 14 is not needed. Examples of graphical output results from analyses conducted by GC system 100 are shown in FIGS. 7 and 8. Detector 106 can be any type of detector, including but not limited to flame ionization detectors (FID), photoionization detectors (PID), helium ionization detectors (HID), thermal conductivity detectors (TCD), flame photometric detectors (FPD), nitrogen-phosphorus detectors (NPD), or mass spectrometers (MS).

Figure 4:
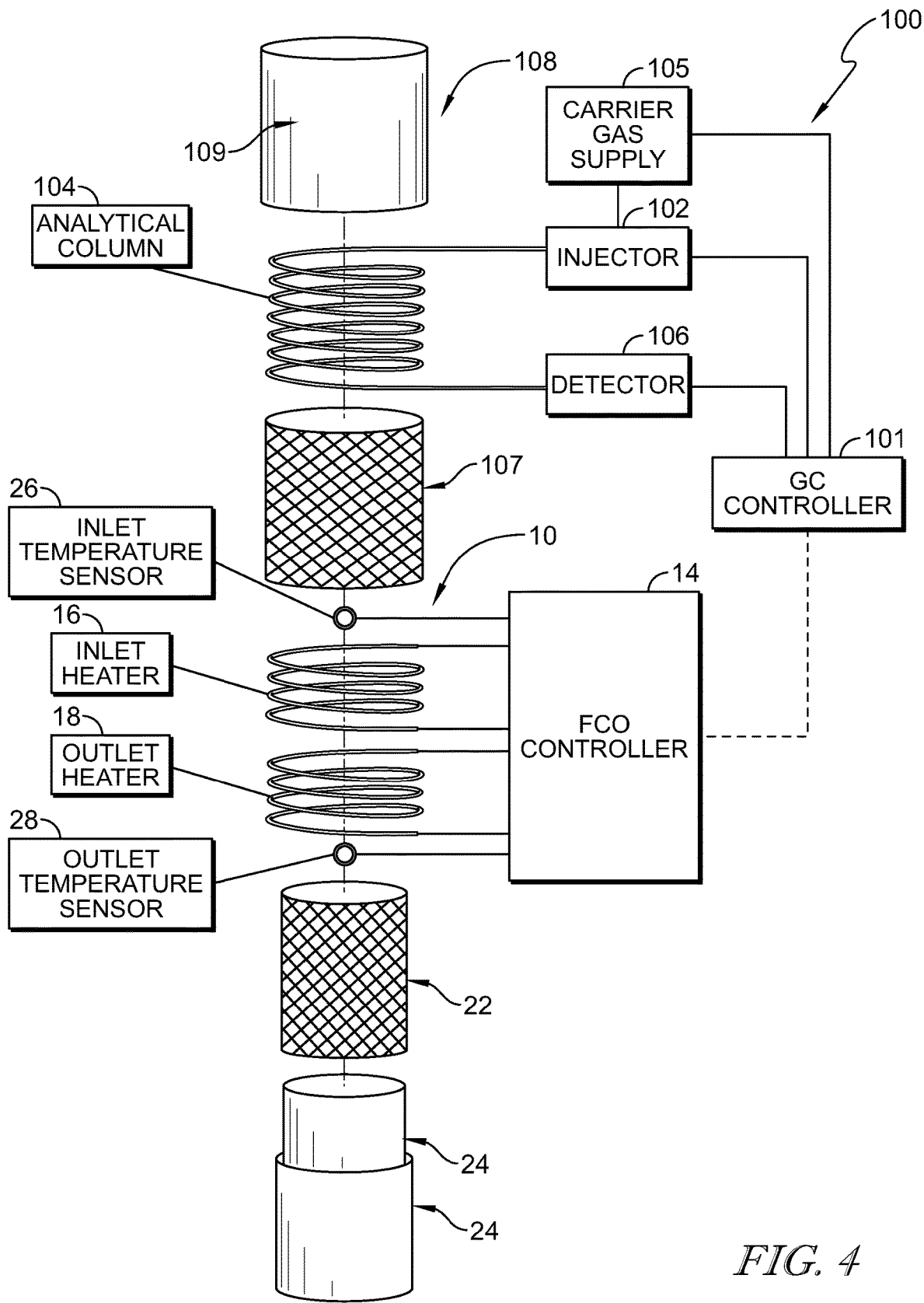
FIG. 4 is an exploded assembly view of the GC system of FIG. 3 showing that the fluidless column oven includes a support frame arranged to receive inlet and outlet heaters thereon and suggesting that the inlet heater is configured to define an inlet portion of the temperature profile along the column and the outlet heater is configured to define an outlet portion of the temperature profile.

In one illustrative embodiment, FCO 10 includes an inlet heater 16 and an outlet heater 18 as shown in FIG. 4. Inlet heater 16 is configured to form heat zones 12 along inlet portion 11 of analytical column 104 and outlet heater 18 is configured to form heat zones 12 along outlet portion 13. Inlet and outlet heaters 16, 18 are mounted on a heater support frame 22. In some embodiments, heater support frame 22 is a low-mass metal screen formed in the shape of a cylinder. A low-mass metal material, such as stainless steel for example, limits heat conductivity between adjacent heat zones 12 while providing structural stability. Insulation 24 lines the interior and exterior of heater support frame 22.

Inlet and outlet heaters 16, 18 are connected to FCO controller 14 as shown in FIG. 4. An inlet temperature sensor 26 is coupled to heater support frame 22 and positioned along inlet heater 16. Inlet temperature sensor 26 is configured to sense a temperature of a heat zone formed by inlet heater 16, such as heat zone 1 for example, and to communicate the sensed temperature to FCO controller 14 for regulating power supplied to inlet heater 16 Similarly, an outlet temperature sensor 28 is coupled to heater support frame 22 and positioned along outlet heater 18. Outlet temperature sensor 28 is configured to sense a temperature of a heat zone formed by outlet heater 18, such as heat zone 6 for example, and to communicate the sensed temperature to FCO controller 14 for regulating power supplied to outlet heater 18. In some embodiments, inlet and outlet temperature sensors 26, 28 are thermocouples.

Figure 5:
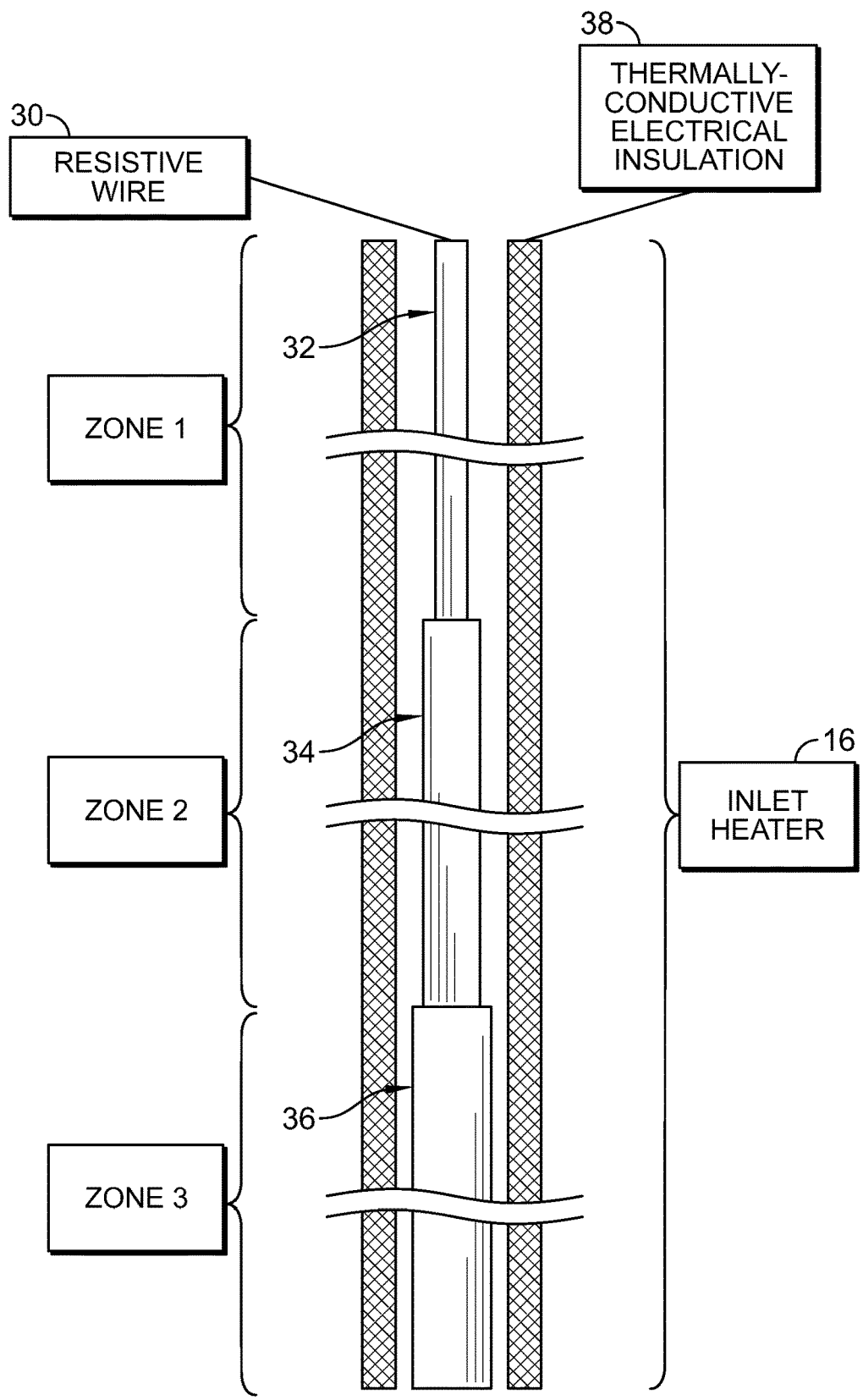
FIG. 5 is an enlarged partial-sectional view of the inlet heater of FIG. 4 showing that the inlet heater includes a plurality of varying sized resistive wires connected end-to-end to define the varying heat zones along an inlet portion of the analytical column and suggesting that voltage applied across the inlet heater will cause the varying sized wires to heat to different temperatures from one another.

One illustrative embodiment of an inlet heater 16 is shown in FIG. 5. A resistive wire 30 includes a plurality of wire sections 32, 34, 36 corresponding to heat zones formed by inlet heater 16. Power applied across resistive wire 30 causes resistive wire 30 to produce heat. Wire sections 32, 34, 36 have varying diameters to provide varying levels of heat for a given power input. For example, wire section 32 has a smaller diameter than wire section 34, and wire section 32 will produce more heat than wire section 34 as power is applied across resistive wire 30 as suggested in FIG. 6. Similarly, wire section 36 has a larger diameter than both wire sections 32, 34, and both wire sections 32, 34 will produce more heat than wire section 36 as power is applied across resistive wire 30. A thermally-conductive electrical insulation 38 extends around resistive wire 30, as shown in FIG. 5, to allow heat to pass through while blocking electrical contact between adjacent sections of inlet heater 16. In some embodiments, thermally-conductive electrical insulation 38 is formed from closely braided continuous filament fiberglass.

Figure 6:
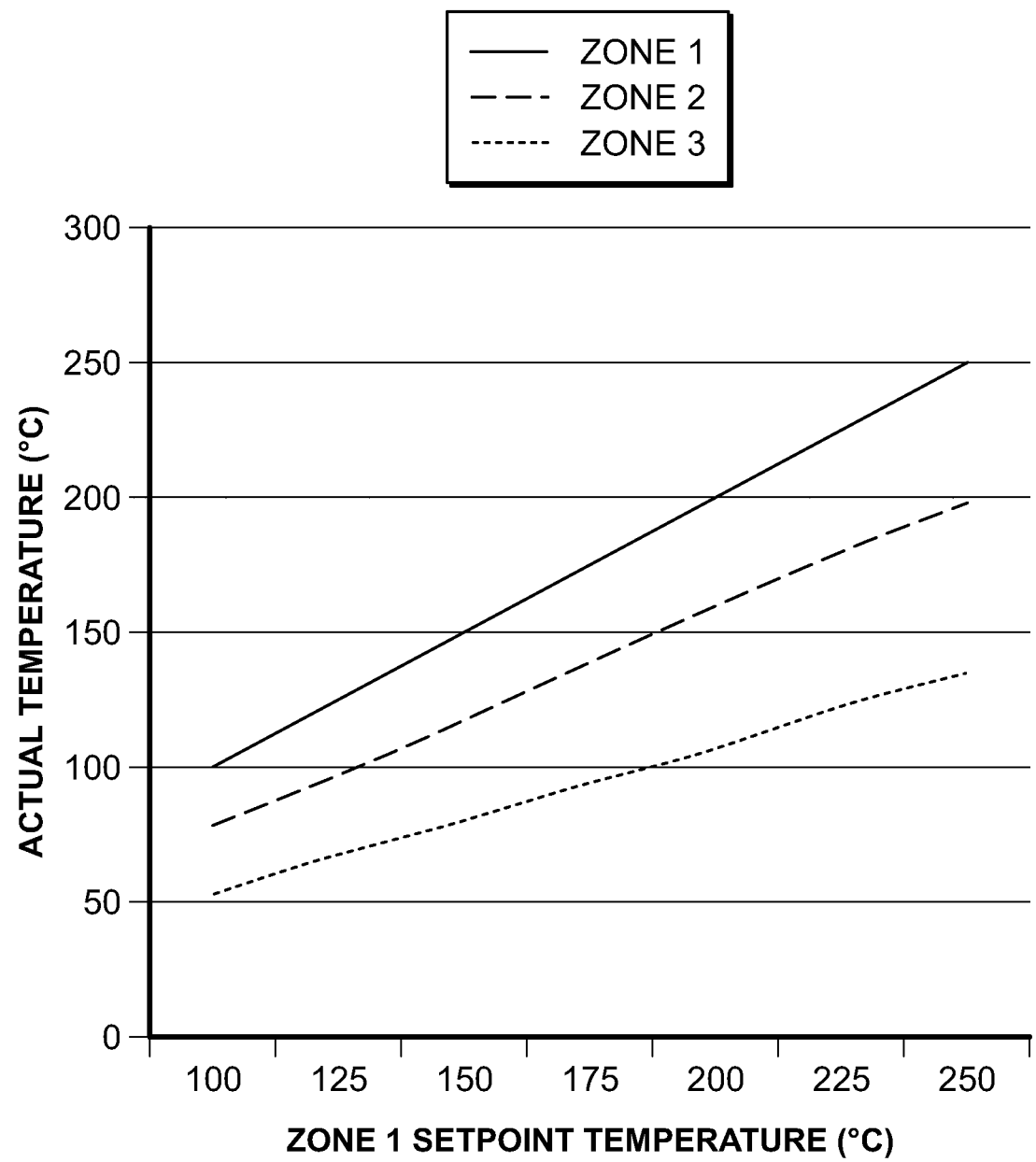
FIG. 6 is a graph showing zone temperatures for the inlet heater of FIG. 5 according to one embodiment of the present disclosure and suggesting that the actual temperatures in various zones can be determined based on a set-point temperature measured from one of the zones and that the inlet portion of the temperature profile along the column can be adjusted based on the set-point temperature.

A temperature in heat zones 2 and 3 can be determined from a set-point temperature of zone 1, as sensed by inlet temperature sensor 26 for example, based on the properties of resistive wire 30 as suggested in FIG. 6. The temperature profile along inlet portion 11 of analytical column 104 can be adjusted based on an amount of power supplied to inlet heater 16. In some embodiments, outlet heater 18 also includes a resistive wire of varying diameter thermally-conductive electrical insulation. Heat produced by outlet heater 18 can be controlled similar to inlet heater 16 using FCO controller 14 and outlet temperature sensor 28.

FCO controller 14 is configured to control an amount of power supplied to inlet heater 16 and outlet heater 18 to maintain a selected temperature profile as suggested in FIG. 2. In some embodiments, FCO controller 14 selectively applies power to inlet and outlet heaters 16, 18 based on temperature signals provided by inlet and outlet temperature sensors 26, 28 as suggested in FIG. 4. Although temperature control by the FCO 10 is fluidless, diffusion of heat through the insulation surrounding FCO 10 will naturally cool FCO 10 and analytical column 104 when power to inlet and outlet heaters 16, 18 is reduced or turned off.

One embodiment of a column assembly 108 is shown in FIG. 4. Column assembly 108 includes a column support frame 107 for supporting analytical column 104 and insulation 109 extending around an exterior of analytical column 104. Column support frame 107 is sized to receive FCO 10 therein so that heat can be applied directly to analytical column 104. In some embodiments, column support frame 107 is a low-mass metal screen formed in the shape of a cylinder.

An exemplary chromatogram in accordance with the present disclosure of a BTEX (benzene, toluene, ethylbenzene, and xylenes) analysis using GC system 100 with FCO 10, installed in a DPS Companion 2 Portable GC system manufactured by DPS Instruments Europe GmbH, with on-column injector and flame ionization detector (FID), according to an example embodiment is shown in FIG. 7. An inlet set-point temperature of 140° C. and an outlet set-point temperature of 45° C. were selected for the analysis. The inlet and outlet temperatures were controlled by standard heat circuits within the DPS Companion 2 Portable GC system such that GC controller 101 of the system was used in place of a stand-alone FCO controller. The FID detector temperature was set to 150° C. to make sure all compounds eluting from analytical column 104 would make it through to detector 106. The gain for the FID was set to 6, with a collector voltage of −100V leading to the amplifier, and subsequent chromatography data system to gather the data. The separation was performed on a 30 meter×0.53 millimeter, 1 micrometer film thickness MXT-1 capillary column using helium as the carrier gas. In some embodiments, FCO 10 can be controlled with the temperature control circuitry found in some commercially available GC systems by connecting the inlet and outlet heaters 16, 18 and temperature sensors 26, 28 thereto. If the circuitry is not available, then FCO 10 can also be controlled by a stand-alone FCO controller 14 as suggested in FIG. 4. The carrier gas control can be made through a standard pressure control circuitry, such as that found in the DPS Companion 2 Portable GC.

The chromatogram results of FIG. 7 show good peak shape and separation in less than 1 minute. With a conventional air bath oven, the same analysis would take approximately 6 minutes, plus an additional 2 minutes for cool down and another 2 minutes for temperature equilibrium, making the total run to run cycle time 10 minutes. Use of FCO 10 provides analyses ten times faster because material samples can be analyzed one right after another without the need for heating and cooling cycles. In some embodiments, 60 material samples per hour can be analyzed using GC system 100. This can be compared to the previous conventional fluid ovens, which could only analyze six material samples per hour. For even faster analyses using FCO 10 according to this disclosure, a shorter and narrower bore column could be installed in GC system 100. Changing the carrier gas to hydrogen would also speed up the analysis.

Gas chromatography system 100 can also be used for higher boiling point, or semi-volatile compounds. An exemplary chromatogram in accordance with the present disclosure of an organochlorine pesticide analysis using GC system 100 with FCO 10, installed in a DPS Companion 2 Portable GC system is shown in FIG. 8. An inlet temperature set-point of 320° C. and an outlet temperature set-point of 180° C. were selected. The same heater control circuitry contained in the DPS GC system, as previously described, was used for this analysis. The FID detector temperature was set to 250° C. to ensure all compounds eluting from analytical column 104 would make it through to detector 106. The gain for the FID was set to 6, with a collector voltage of −100V leading to the amplifier, and subsequent chromatography data system to gather the data. A 30 meter×0.53 millimeter, 1 micrometer film thickness MXT-1 capillary column was used for the separation. This is not the normal column of choice for pesticide analysis and the peak separation is not as good as with a pesticide specific column, but the chromatogram depicts good results using a general purpose 30 meter capillary column when FCO 10 is used. With the aid of a carrier pressure program in GC controller 101, the compounds eluted from in less than 4 min. With this configuration, GC system 100, with FCO 10 installed, is able to perform 15 pesticide analyses per hour. This is an improvement over traditional systems, which typically perform in the range of two pesticide analyses per hour, making GC system 100 more than seven times faster.

Figure 9:
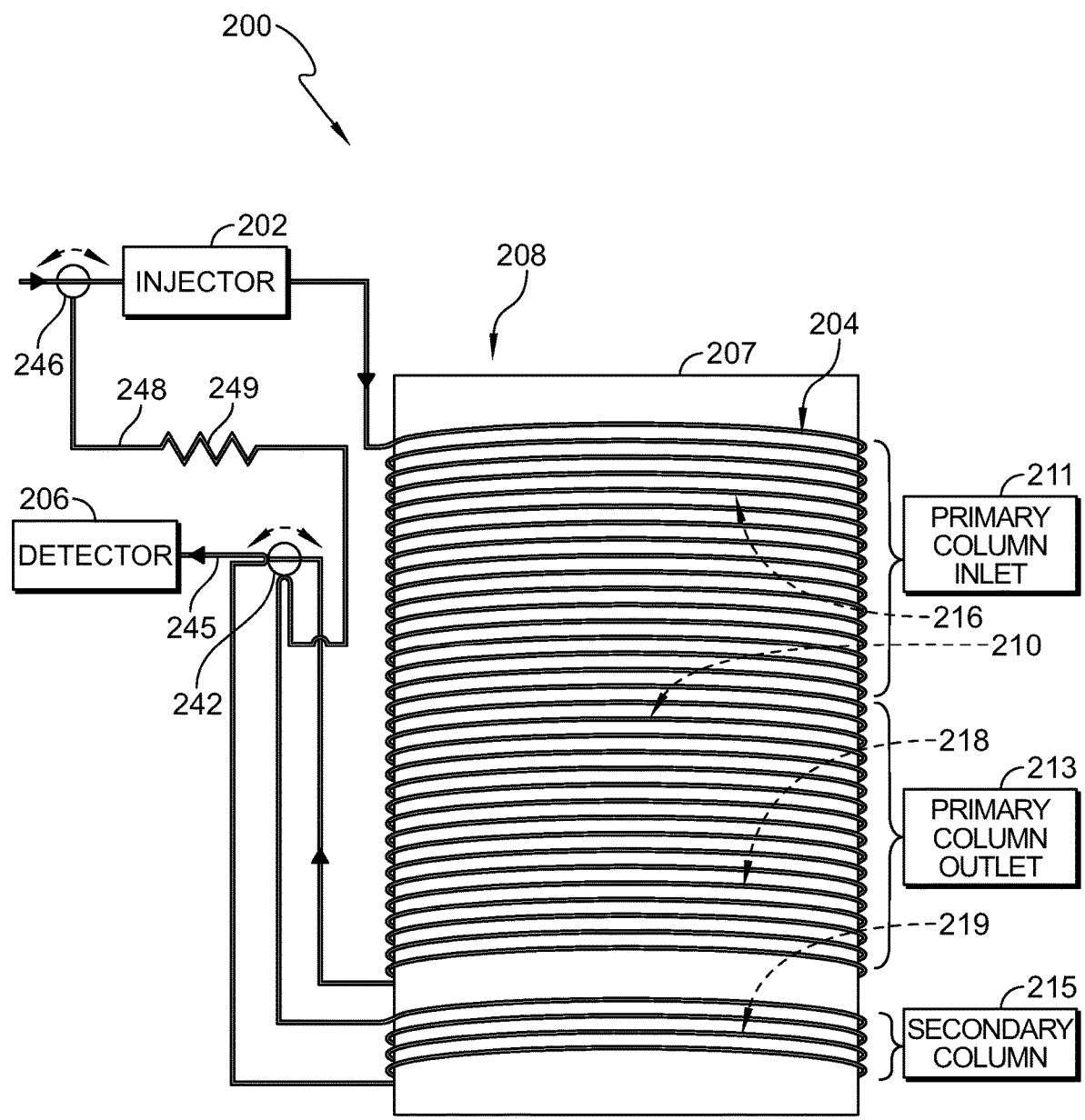
FIG. 9 is a diagrammatic view of another embodiment of a GC system in accordance with the present disclosure showing that an analytical column of the GC system includes a primary column inlet, a primary column outlet, and a secondary column and suggesting that a selector valve is configured to selectively direct the material sample to the detector either directly from the primary column outlet or through the secondary column.

Another embodiment of a gas chromatography system 200 in accordance with the present disclosure is shown in FIG. 9. GC system 200 includes an injector 202 coupled to an analytical column 204 for sending a sample of material to be analyzed toward a detector 206. A fluidless column oven 210 of GC system 200 forms a plurality of heat zones to define a temperature profile along analytical column 204 as suggested in FIG. 12. Analytical column 204 extends around a column support frame 207 as part of a column assembly 208.

Analytical column 204 includes a primary column inlet 211, a primary column outlet 213, and a secondary column 215 as shown in FIG. 9. Primary column inlet 211 is coupled to injector 202 for receiving the material sample. A selector valve 242 connects primary column outlet 213 and secondary column 215 with detector 206 by a transfer line 245. Selector valve 242 is configured to direct the material sample exiting primary column outlet 213 to detector 206 or through secondary column 215 at the selection of a user of GC system 200 as suggested in FIGS. 9-11. Selector valve 242 is shown in an open position in FIG. 10 to direct the material sample to detector 206, and selector valve 242 is shown in a closed position in FIG. 11 to direct the material sample through secondary column 215 before arriving at detector 206. Directing a portion of effluent from a primary column to a secondary column for further separation is sometimes called a 2-dimensional ("2D") analysis.

Figure 12:
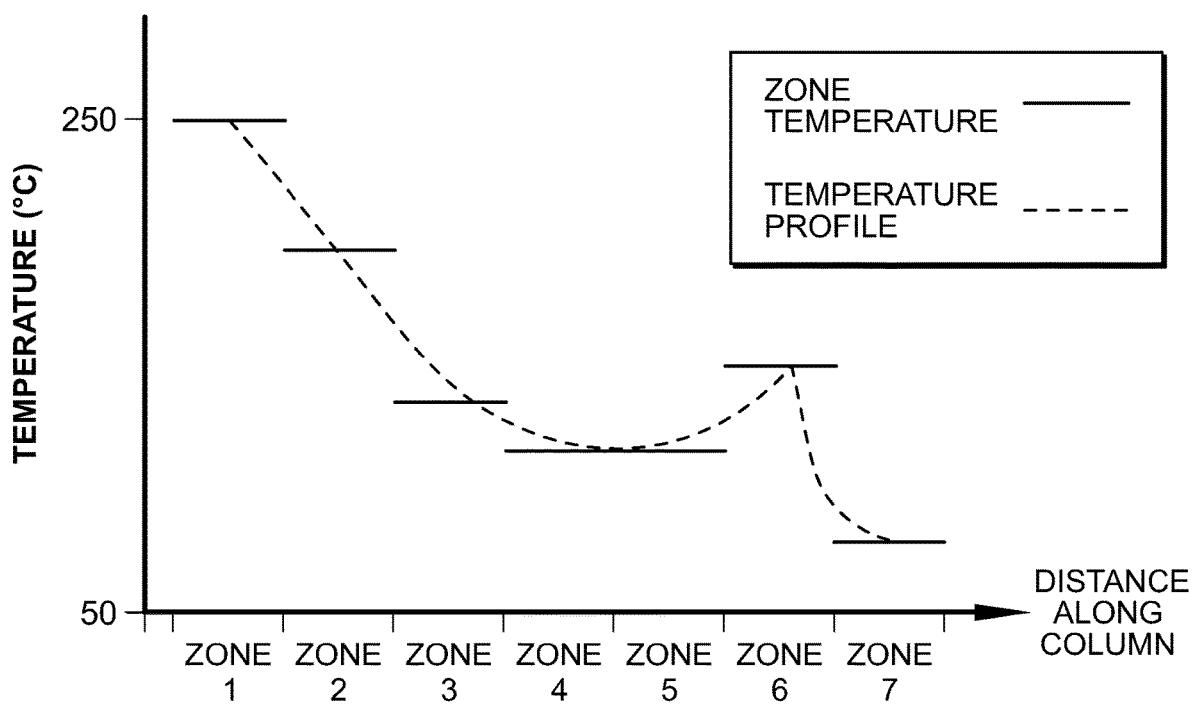
FIG. 12 is a graph showing another embodiment of a temperature profile in accordance with the present disclosure defined by varying temperatures in heat zones of the GC system of FIG. 9 and suggesting that the secondary column is arranged in a heat zone at a lower temperature than the heat zone of the primary column outlet.

Fluidless column oven 210 includes an inlet heater 216 extending along primary column inlet 211 of analytical column 204, an outlet heater 218 extending along primary column outlet 213, and a secondary heater 219 extending along secondary column 215 as suggested in FIG. 9. In some embodiments, outlet heater 218 extends along both primary column outlet 213 and secondary column 215 in place of a stand-alone secondary heater 219. One embodiment of a temperature profile defined by FCO 210 in accordance with the present disclosure is shown in FIG. 12. In the illustrative embodiment, FCO 210 is configured to form seven heat zones positioned along analytical column 204 with zones 1-3 positioned along primary column inlet 211, zones 4-6 positioned along primary column outlet 213, and zone 7 positioned along secondary column 215. Each of heat zones 1-7 can be adjusted to have the same or different temperatures compared to an adjacent heat zone. The temperature profile, as defined by the heat zones of FCO 210, includes a negative temperature gradient portion, such as along primary column inlet 211, and a subsequent positive temperature gradient portion, such as along primary column outlet 213, based on varying temperatures between the heat zones 1-6. In some embodiments, the temperature profile includes a positive temperature gradient portion and subsequent negative temperature gradient portion. In some embodiments, the temperature profile has an overall negative temperature gradient or an overall positive temperature gradient. In some embodiments, the temperature profile has a temperature gradient of substantially zero.

In the illustrative embodiment, the temperature of zone 7, for secondary column 215, is lower than zones 4-6 for primary column outlet 213 as suggested in FIG. 12. In some embodiments, an analysis conducted using GC system 200 begins with selector valve in the closed position to allow lighter constituent compounds in the material sample to elute from the primary column outlet 213 and pass through secondary column 215 before arriving at detector 206. Later in the analysis, selector valve 242 is returned to the open position to direct heavier constituent compounds eluted from the material sample from primary column outlet 213 to detector 206 without passing through secondary column 215. The lighter constituent compounds passing through secondary column 215 are exposed to the lower temperature of heat zone 7, while the heavier constituent compounds are exposed to the higher temperature heat zone 6 before passing to detector 206. Two different detector temperatures are useful for analyses containing both volatile and semi-volatile compounds.

Figure 10:
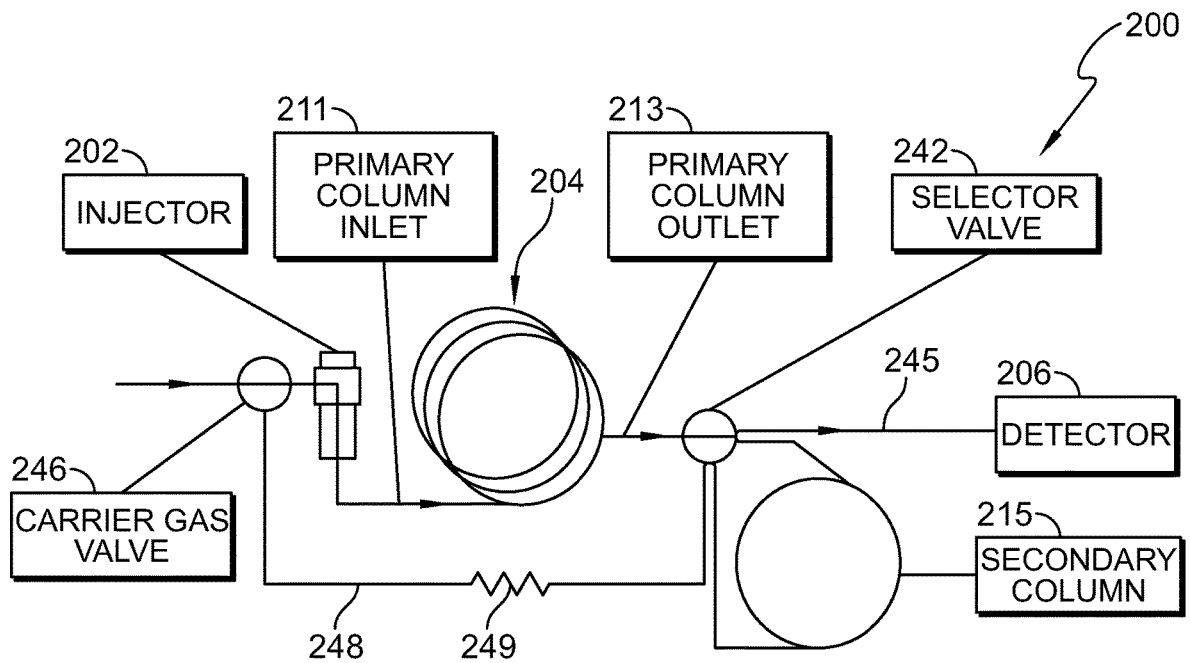
FIG. 10 is a diagrammatic view of the GC system of FIG. 8 showing the selector valve in an open position to direct the material sample through the primary column outlet to the detector.
Figure 11:
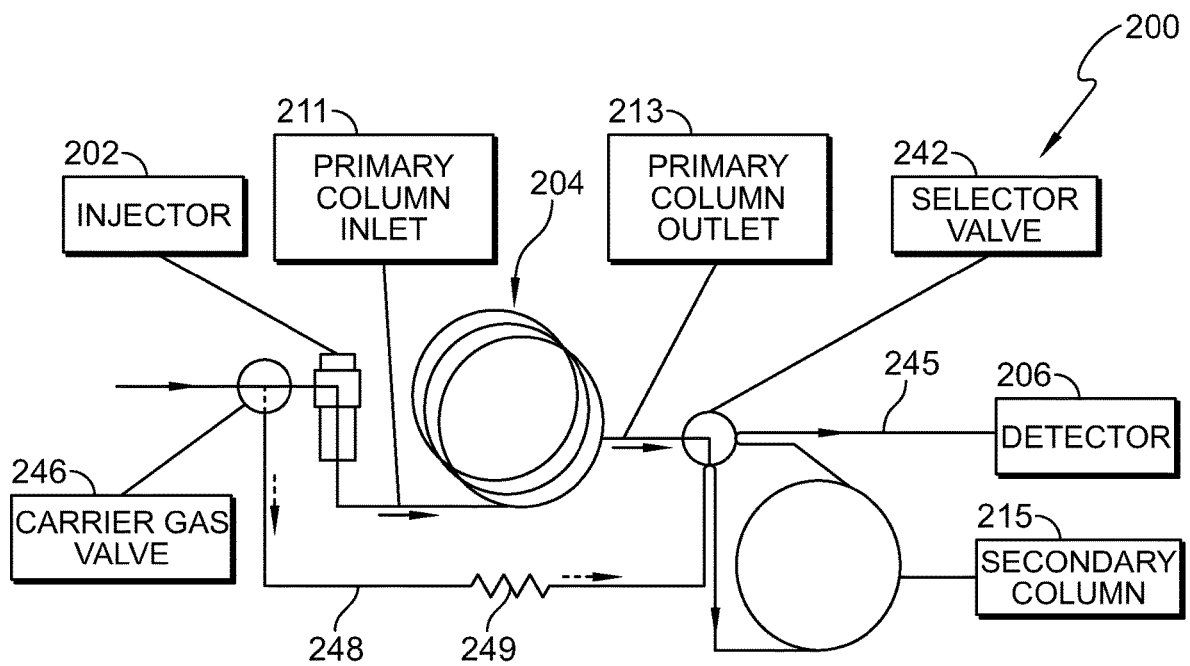
FIG. 11 is a view similar to FIG. 10 showing the selector valve in a closed position to direct the material sample from the primary column outlet through the secondary column to the detector and suggesting that a carrier gas valve may be used to bypass the primary column, thereby stopping the flow of material sample through the primary column, and directing carrier gas to the secondary column.

A carrier gas valve 246 is coupled to injector 202 and to selector valve 242 by a bypass line 248 as shown in FIGS. 9-11. Carrier gas valve 246 is configured to direct carrier gas used during a GC analysis through the injector 202 (and to primary column inlet 211) or through bypass line 248 to selector valve 242 at the selection of a user of GC system 200. A restrictor 249 is coupled to bypass line 248 and forms, in combination with secondary column 215, a similar restriction to flow as that from primary column inlet 211 to primary column outlet 213 to maintain a constant flow of carrier gas through GC system 200. In the illustrative embodiment, selector valve 242 is a three-way valve having five connections points for connecting to bypass line 248, primary column outlet 213, an inlet and an outlet of secondary column 215, and transfer line 245. Carrier gas valve 246 can also be a three-way valve, but with three connections to a carrier gas supply (not shown in FIGS. 9-11), injector 202, and bypass line 248.

In one illustrative embodiment, carrier gas and the material sample are sent through injector 202, through primary column 204, and to detector 206 through selector valve 242 in the opened position as suggested in FIG. 10. Selector valve 242 is moved to the closed position to direct at least a portion of the material sample into secondary column 215 as suggested by the solid line arrows in FIG. 11. Carrier gas valve 246 can be actuated to send carrier gas through bypass line 248 to stop the flow of the material sample through primary column 204 while continuing flow through secondary column 215 as suggested by the dashed line arrows in FIG. 11.

When the analysis is started, selector valve 242 is actuated to the closed position such that the solvent and lighter boiling point compounds are directed to secondary column 215 in heat zone 7. This adds to a length of travel of the material sample to further separate these compounds at a lower secondary column temperature. The additional travel requires more time for the separation and a three-way carrier gas bypass valve 205 is used to stop the travel of material sample through primary column 204 while the secondary column 215 is performing the additional 2-dimensional separation. The carrier gas bypasses the primary column 204 and is directed to the secondary column 215 via the selector valve 242. An example of the material sample in primary column 204 being stopped is shown in FIG. 14 where the C16 peak on the chromatogram is 0.7 min later than in FIG. 13, which directly corresponds to the time that the carrier gas bypass valve 205 was actuated. Once the secondary column 215 has performed the additional separation the selector valve 242 is actuated to the open position and the carrier gas bypass valve 205 is actuated to the open position, allowing the rest of the compounds in the analytical column 204 to elute through the higher outlet temperature in heat zone 6.

Carrier gas valve 246 can be controlled independently of selector valve 242. The carrier gas can bypass to secondary column 215 with selector valve 242 in either the open or closed position. Selector valve 242 can be actuated one or more times during an analysis to direct portions of the material sample from primary column outlet 213 to secondary column 215. Similarly, carrier gas valve 246 can be actuated one or more times during the analysis to stop the flow of the material sample through primary column 204. Selector valve 242 is maintained at the higher inlet temperature in heat zone 2 minimizing any potential carry-over. Actuation of valve 242 does not affect the temperature profile, so one material sample can still be analyzed immediately after another.

Figure 13:
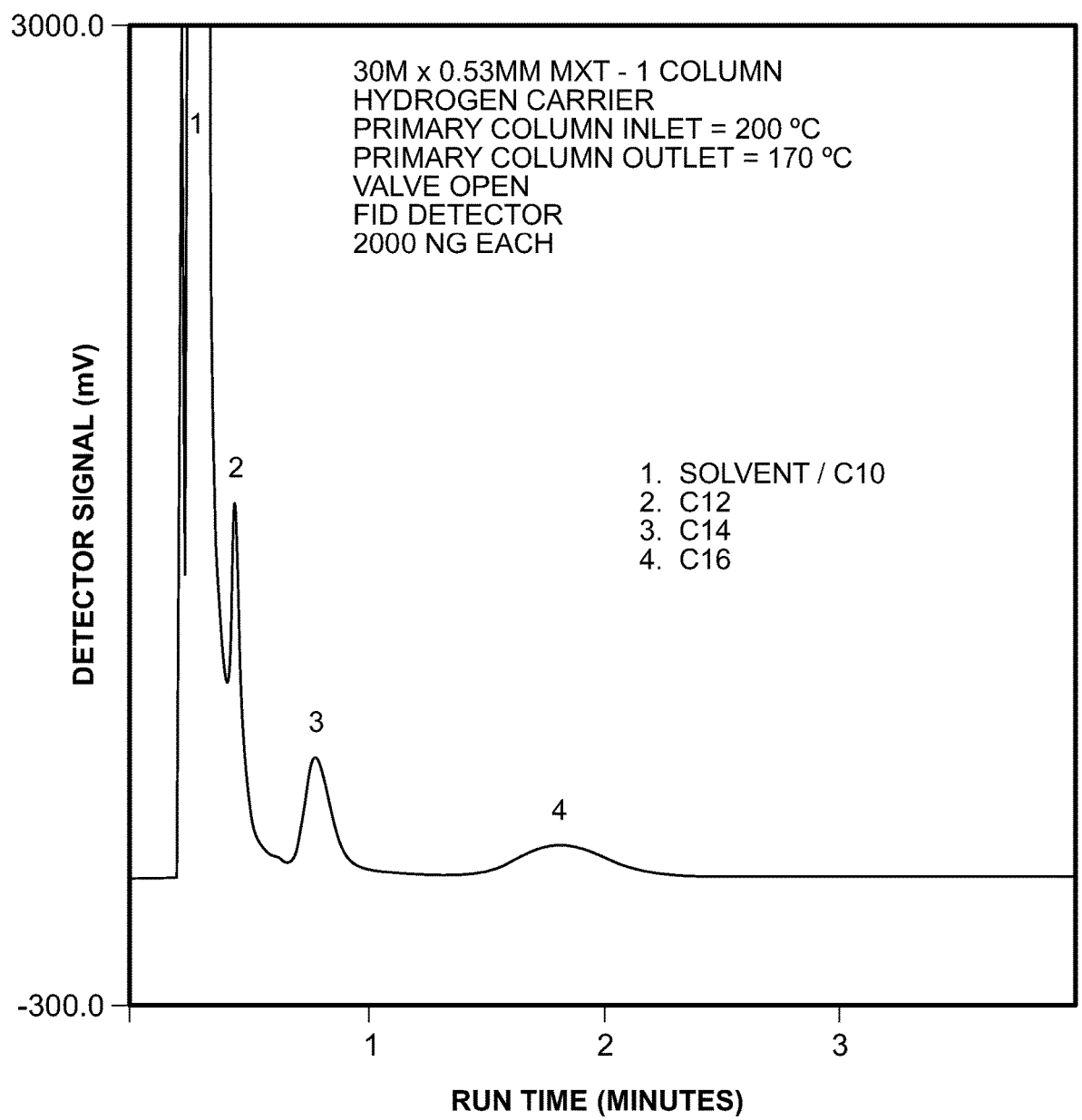
FIG. 13 is a chromatogram of a n-alkane hydrocarbon analysis using a GC system in accordance with the present disclosure whereby the sample is directed through the primary outlet portion of the column to the detector.
Figure 14:
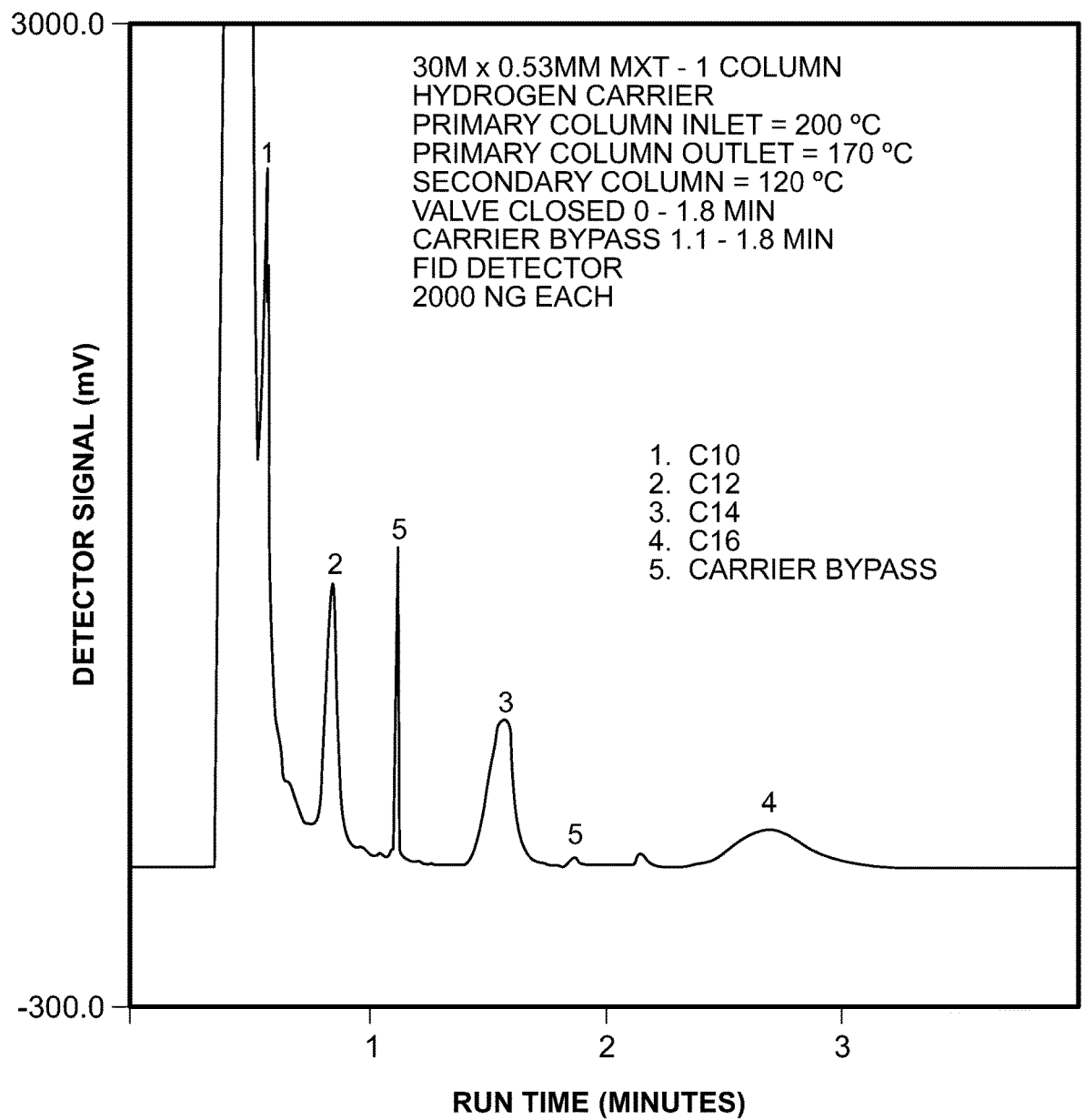
FIG. 14 is a chromatogram of a n-alkane hydrocarbon analysis using a GC system in accordance with the present disclosure whereby the sample is directed through the primary column outlet and then through the secondary column for additional 2-dimensional separation of the material sample.

Exemplary chromatograms in accordance with the present disclosure of an n-alkane hydrocarbon analyses using GC system 200 with FCO 210 installed in a DPS Companion 2 Portable GC system are shown in FIGS. 13 and 14. A primary column inlet temperature set-point of 200° C. and a primary column outlet temperature set-point of 170° C. were selected. The same heater control circuitry contained in the DPS GC system, as previously described, was used for this analysis. Additionally, carrier gas valve 246 and the selector valve 242 were controlled through the DPS GC system; thereby making this an example of the GC controller 101 within the DPS GC system acting in place of stand-alone FCO 2D controller 214. The FID detector temperature was set to 250° C. to ensure all compounds eluting from analytical column 204 would make it through to detector 106. The lower gain of 4 was set for the FID due to the higher concentration sample, with a collector voltage of −100V leading to the amplifier, and subsequent chromatography data system to gather the data. A 30 meter×0.53 millimeter, 1 micrometer film thickness MXT-1 capillary column was used for the separation and hydrogen was selected as the carrier gas.

FIG. 13 is an example of a separation using primary column 204 only, wherein the C10 peak is merged with the solvent peak. FIG. 14 demonstrates further 2-dimensional separation of the same material sample, wherein the C10 peak is separated from the solvent with a secondary column 215 temperature of 120° C. In this embodiment, secondary column 215 was a short 4-meter section of the same column used for primary column 204 and contained within heat zone 7. Heat zone 7 was formed by outlet heater 218. With a primary outlet heater 218 set-point of 170° C., heat zone 7 followed with a temperature of 120° C. To complete the 2D analysis, selector valve 242 and carrier gas valve 246 were actuated during the times shown in FIG. 14.

Figure 15:
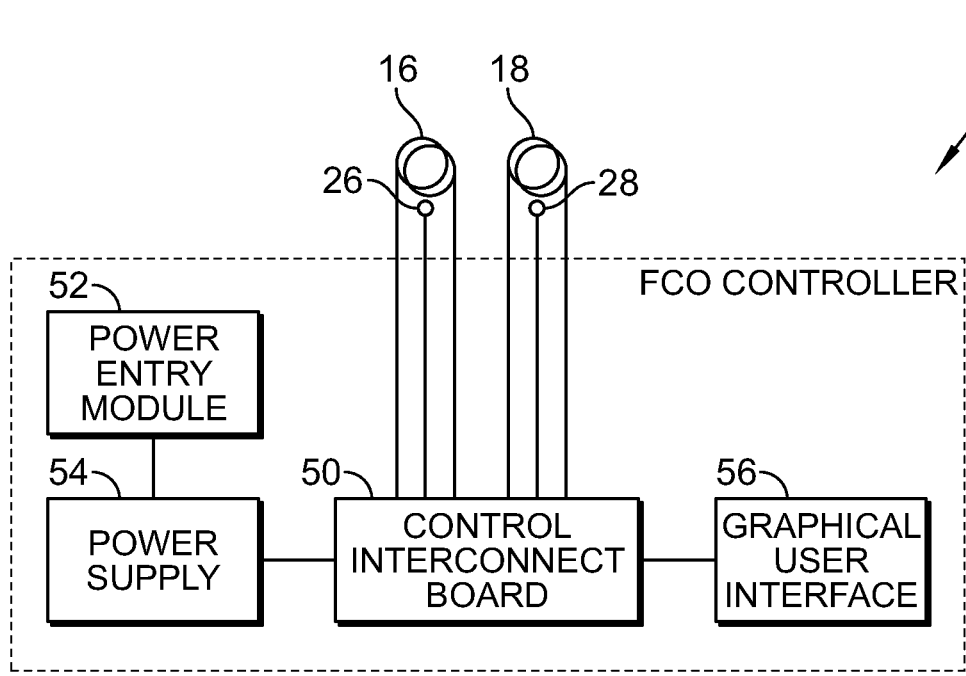
FIG. 15 is diagrammatic view of one embodiment of a FCO controller in accordance with the present disclosure for use in the GC system of FIG. 4.

In one illustrative embodiment, FCO controller 14 includes a control interconnect board 50, a power entry module 52, a power supply 54, and a graphical user interface 56 as shown in FIG. 15. Control interconnect board 50 includes temperature control circuitry to control temperatures of inlet heater 16 and outlet heater 18, and to accept input from inlet temperature sensor 26 and outlet temperature sensor 28. Wired and wireless connections for the heaters 16, 18 and temperature sensors 26, 28, can be used. Power entry module 52 includes various power components, such as a power switch, electrical connections, filters (e.g., line filters), and/or circuit breakers. Power supply 54 provides power (e.g., to provide power for the heaters 16, 18, graphical user interface 56, or other components). Graphical user interface 56 can be used to set the inlet and outlet set-point temperatures, among other uses. FCO controller 14 can be integrated into a GC system controller. Alternatively or additionally, FCO 10 and FCO controller 14 can be stand-alone components, which could be used to make almost any GC or GC/MS system a fast GC system in accordance with the present disclosure.

Figure 16:
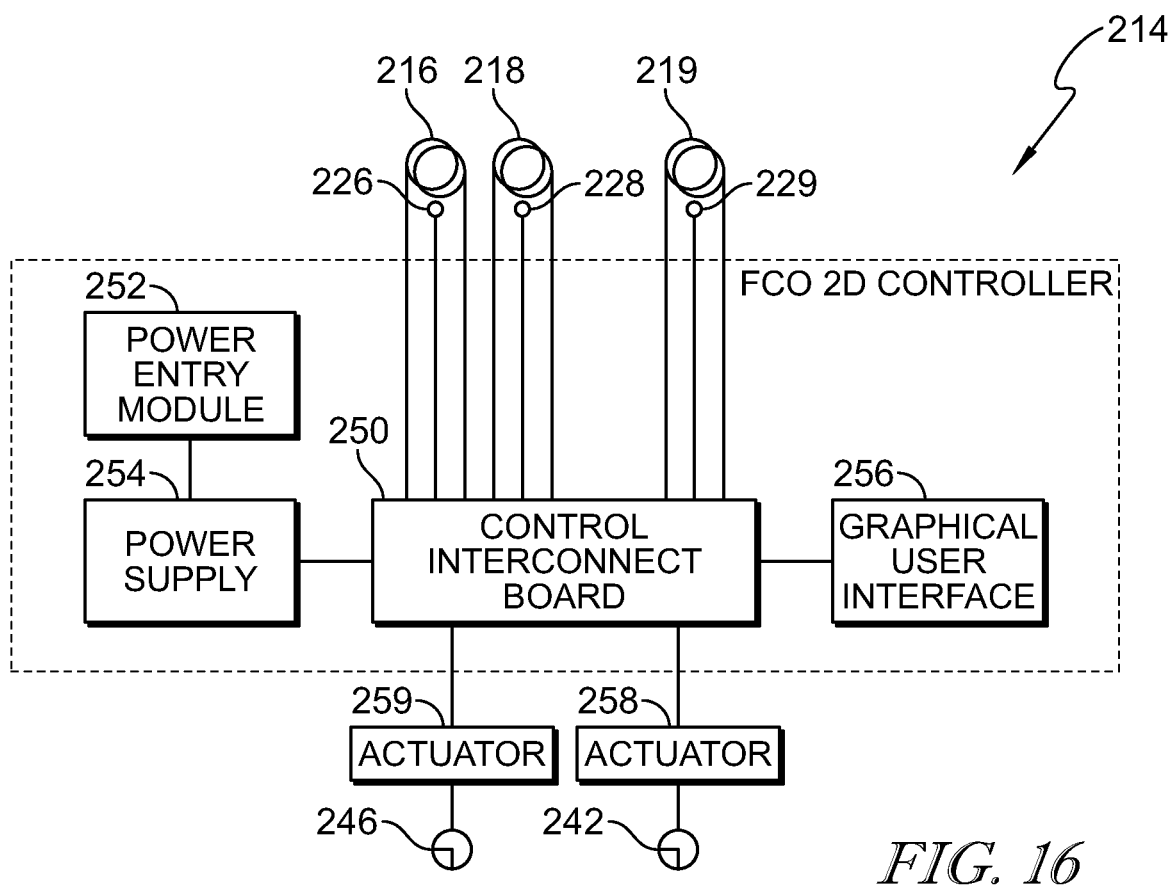
FIG. 16 is diagrammatic view of one embodiment of a FCO 2D controller in accordance with the present disclosure for use in the GC system of FIG. 9.

One illustrative embodiment of a FCO 2D controller for use in GC system 200 is shown in FIG. 16. FCO 2D controller 214 includes a control interconnect board 250, a power entry module 252, a power supply 254, and a graphical user interface 256. Control interconnect board 250 includes temperature control circuitry to control temperatures of inlet heater 216, outlet heater 218, and secondary (2D) heater 219, and to accept input from the inlet thermocouple 226, the outlet thermocouple 228, and a secondary (2D) thermocouple 229 positioned adjacent to secondary heater 219. Control interconnect board 250 also connects with actuators 258, 259 of selector valve 242 and carrier gas valve 246, respectively, to control actuation of selector valve 242 and carrier gas valve 246. In some embodiments, valve actuator 258 actuates selector valve 242, such as by rotation. In some embodiments, valve actuator 259 actuates carrier gas valve 246. In some embodiments, valve actuator 259 is a solenoid. Wired and wireless connections for the heaters 216, 218, 219, temperature sensors 226, 228, 229, and valve actuators 258 and 259 can be used. Power entry module 52 includes various power components, such as a power switch, electrical connections, filters (e.g., line filters), and/or circuit breakers. Power supply 54 provides power (e.g., to provide power for the heaters 216, 218, 219, graphical user interface 256, valve actuators 258, 259, or other components). Graphical user interface 256 can be used to set the inlet and outlet set-point temperatures, and timed events for valve actuations, among other uses. FCO 2D controller 214 can be integrated into a GC system controller. Alternatively or additionally, FCO 210 and FCO 2D controller 214 can be stand-alone components, which could be used to make almost any GC or GC/MS system a fast GC system in accordance with the present disclosure.

Figure 17:
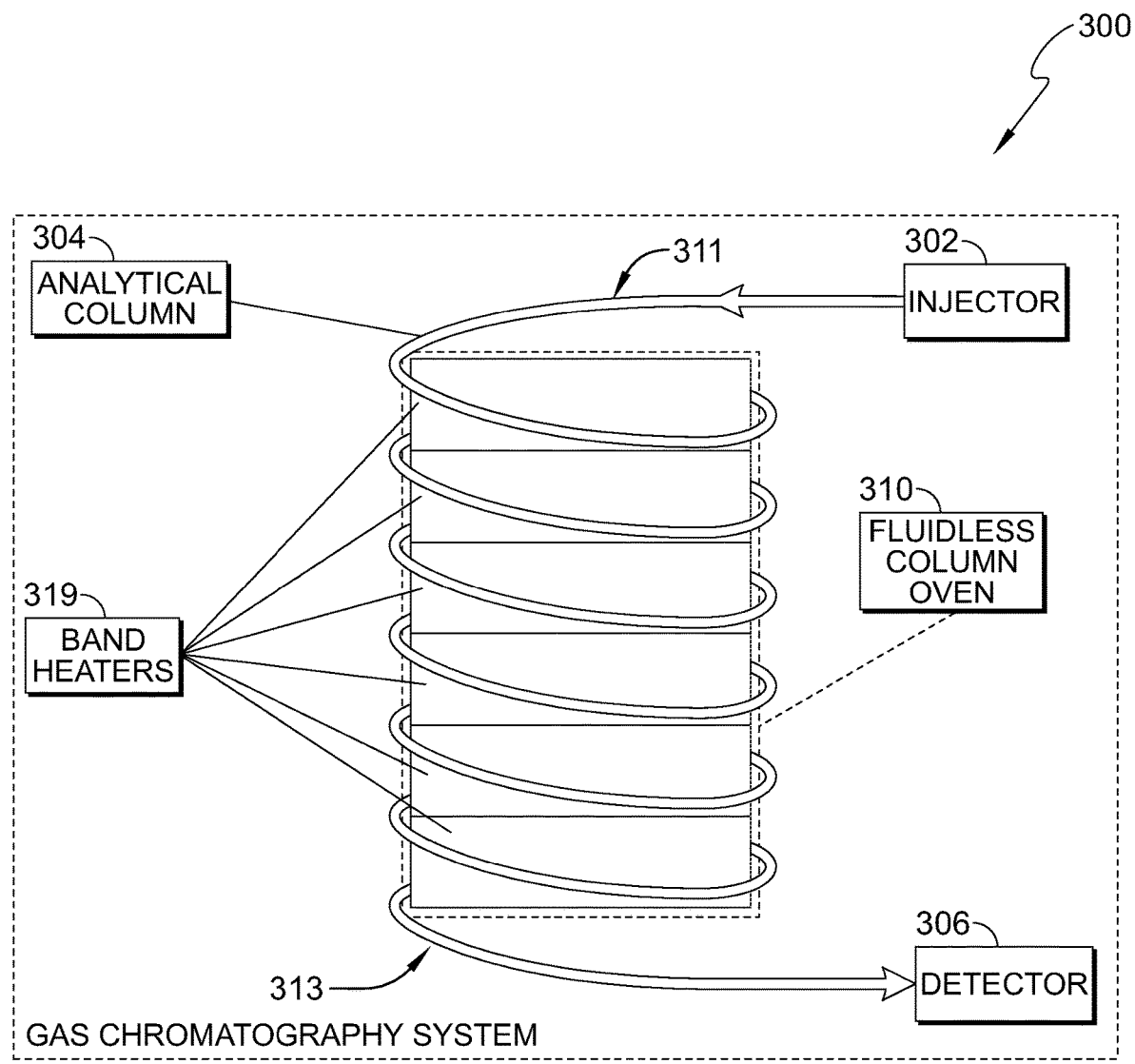
FIG. 17 is a diagrammatic view of another embodiment of a GC system in accordance with the present disclosure showing that the GC system includes a plurality of band heaters arranged along an analytical column and suggesting that the band heaters are independently adjustable relative to one another to adjust a temperature profile along the column.

Another embodiment of a gas chromatography system 300 in accordance with the present disclosure is shown in FIG. 17. GC system 300 includes an injector 302 coupled to an analytical column 304 for sending a sample of material to be analyzed toward a detector 306. A fluidless column oven 310 of GC system 300 forms a plurality of heat zones to define a temperature profile along analytical column 304. Analytical column 304 includes an inlet portion 311 coupled to injector 302 and an outlet portion 313 coupled to detector 306.

Fluidless column oven 310 includes a plurality of band heaters 319 positioned along analytical column 304 as shown in FIG. 17. Each band heater 319 is configured to provide a heat zone and is independently controllable relative to the other band heaters 319. Temperatures of each heat zone can be adjusted to provide different temperature profiles along analytical column 304. In some embodiments, the temperature profile includes a negative temperature gradient portion, such as along inlet portion 311, and a subsequent positive temperature gradient portion, such as along outlet portion 313. In some embodiments, the temperature profile includes a positive temperature gradient portion and subsequent negative temperature gradient portion. In some embodiments, the temperature profile has an overall negative temperature gradient or an overall positive temperature gradient. In some embodiments, the temperature profile has a temperature gradient of substantially zero.

In illustrative embodiments, systems and methods are disclosed for obtaining fast gas chromatography (GC) analysis by positioning a fluidless column oven (FCO) inside a GC system, where heated zones transfer a temperature profile onto the analytical column. The FCO includes a series of resistively heated temperature zones, providing various combinations of isothermal, negative, and positive temperature gradient profile regions. Temperature control circuits for the heated zones and insulation surrounding the heaters and analytical column maintain a steady-state temperature profile on the analytical column. No fluid is used to cool the analytical column between analyses, providing for fast analyses by eliminating the normal heating and cooling cycles found in conventional analytical fluid ovens.

In illustrative embodiments, a temperature profile along the column 104 is created using heaters 16, 18 connected to closed loop heating circuits. When two or more heaters 16, 18 are used in conjunction with one another, both positive and negative temperature gradients can be formed. These temperature gradients can then be used to place various temperatures on different portions of the column 104, creating the column temperature profile. The temperature profile on the column 104 is maintained in a steady state condition permitting one analysis to be performed immediately after another. Although the column temperature control is fluidless, diffusion of heat through the insulation surrounding the FCO 10 will naturally cool the column 104 when the power to the heating elements 16, 18 is reduced or turned off.

In illustrative embodiments, the fluidless column oven 10 is a device designed to reduce the limitations previously found in fast GC devices and fluid oven GC devices. For example, the FCO 10 allows for the use of packed columns, micro-packed columns, and long (e.g., 30 or 60 meter) capillary columns, with no limitation on column bore sizes, by (i) maintaining the column in a constant temperature profile, (ii) by eliminating the temperature ramp portion of the analysis cycle, (iii) by eliminating the cool down portion of the cycle, (iv) eliminating the equilibrium, or rest time, between analyses, and (v) achieving temperature stability equal to an isothermal run. Analysis times using a GC system 100 with the FCO 10 are reduced by a factor of 5 to 10 in comparison to other methods of column heating.

In illustrative embodiments, the FCO 10 does not interfere with the injector 102 of the GC system 100 such that most standard injectors can be used, for example, on-column, split/splitless, and programmed temperature vaporization. Further, such embodiments do not interfere with the position, installation, or function of auto-injectors or concentration devices connected to GC systems, such as headspace, purge & trap, or air concentrators, which pre-concentrate material samples before injection. Large volume gas sample injections, or gas sample valve injections, are also permitted, and the injection volume depends only on the loading capacity of the column selected. The FCO 10 also does not interfere with the GC detector 106 allowing all common detectors, or a mass spectrometer, to be used for the detection system.

In illustrative embodiments, the FCO 10 includes an inlet heater assembly 16, an outlet heater assembly 18 using a heater element 30, an inlet thermocouple 26, an outlet thermocouple 28, an electrical insulating sheath 38, inlet heater terminating wires, outlet heater terminating wires, and a heater support frame 22. The FCO 10 forms heat zones 12 along the column. The heater support frame 22 is a low mass metal screen in the shape of a cylinder. Both sides of the heater support frame 22 are insulated to prevent heat transfer between heat zones 12 through the metal support frame. The diameter, or shape, of the heater support frame 22 can be of various sizes to fit specific column types. For metal capillary columns, which can be coiled as small as 3.5 inches, the diameter of the heater support frame 22 can be small, for example, approximately as small as 2.5 inches. A FCO 10 with a 30 meter metal capillary column is small enough to be installed in small oven and portable GC systems, such as the DPS Companion manufactured by DPS Instruments Europe GmbH. A larger diameter heater support frame 22 may be needed for other columns, such as wide bore fused silica capillary columns, which require a larger column coil to avoid stressing and breaking the column.

In illustrative embodiments, the inlet heater assembly 16 can be formed of heating element portions 32, 34, 36 that are wrapped or coiled around the top of the heater support frame 22. In some embodiments, the inlet heater assembly 16 heating element 30 can form a single heat zone, or multiple heat zones, to control the temperature profile for the inlet heater assembly 16. A single heat zone would form an isothermal profile on that portion of the column 104. For finer temperature control, additional heating elements or varying heating elements can be used to create a plurality of heat zones of differing heating values. When a subsequent or adjacent heat zone has a lower heating value than the previous one, a negative temperature gradient will be formed. When a subsequent or adjacent heat zone has a higher heating capacity than the previous, a positive temperature gradient will be formed in that section of the temperature profile on the column 104.

In illustrative embodiments, three heat zones are formed by three heating element portions 32, 34, 36 that are attached end to end to form the inlet heater assembly 16. In some embodiments, the heating element portions 32, 34, 36 of inlet heater assembly 16 can be attached end to end for convenience. Alternatively or additionally, each heat zone could be separated into three individual zones (heater and thermocouple device) and controlled using three temperature control circuits. Three heat zones are combined into a single heating assembly for simplicity and ease of use in programming for the user, such as a GC analyst. Each heat zone 12 can have a different heater element portions 32, 34, 36 and heating capacity. The heater element portions 32, 34, 36 can be resistance wires with varying diameters. These resistance wires can be connected end to end via various methods. For example, the resistance wires can be crimped inside an electrical connector, welded using silver solder, or other bonding agent, or spot welded. Other types of heaters can also be used. For example, a FCO could use band heaters (such as FCO 310), heater ropes along one or more heat zones, or any other type of non-fluid heating device. The various heaters types can also create one or more heat zones, and heat zones can be associated with a thermocouple and control circuit. In some embodiments, the heating capacity of earlier heat zones is greater than the heating capacity of later heat zones to form a negative temperature gradient for the inlet heater assembly 16.

In illustrative embodiments, a thermocouple 26 (or thermistor or other temperature sensor) is secured to the heater support frame 22 between heater coils to measure the temperature in the first heat zone. The temperature at the thermocouple 26 can be referred to as the inlet temperature of the compounds being injected into the analytical column 104. The inlet terminating wires connect at ends of the inlet heater assembly 16 to the heater controller circuit in the FCO controller 14 on the control interconnect board. The heater controller circuit and thermocouple 26 can be used to form a closed loop temperature control circuit. The electrical insulating sheath 38 surrounds the heating element 30. The electrical insulating sheath 38 mitigates contact between adjacent portions of the heating element portions 32, 34, 36, the thermocouple 26, and the column support frame 107.

In illustrative embodiments, the outlet heater assembly 18 can be formed from heating elements that are wrapped or coiled around the bottom of the heater support frame 22. Similar to the inlet heater assembly 16, the outlet heater assembly 18 can form a single heat zone, or multiple heat zones, to control the temperature profile for the outlet heater assembly 18. A single heat zone would form an isothermal profile on that portion of the column 104. Additional heating elements or varying heating elements can be used to create a plurality of heat zones of differing heating values. In some embodiments, there are three heat zones, and optionally a fourth heat zone, that are formed by heating elements attached end to end, which form the outlet heater assembly 18. The outlet heater assembly 18 is formed via resistance wires attached end to end for convenience. However, each heat zone could be separated into an individual heat zone (heater and thermocouple device) and could be controlled using separate temperature control circuits. Four heat zones are combined into one heating assembly for simplicity and ease of use in programming for the user, such as a GC analyst. In some embodiments, heat zones can use the same heating element portions to get the same heating capacity. For example, two adjacent heat zones can use the same heating element and heating capacity, which is lower than the heating capacity of a later heating element portion. This forms a positive temperature gradient for the outlet heater assembly 18.

In illustrative embodiments, a negative temperature gradient for the inlet heater assembly 16 and a positive temperature gradient for the outlet heater assembly 18 are used. In some embodiments, a single temperature gradient or other combinations of temperature gradients (e.g., negative-positive-positive or negative-positive-negative) can be used. The use of the selector valve 242 to switch the effluent from the primary column outlet 213 of the column 204 to a secondary column 215, such as a short piece of analytical column at a lower temperature, is an example of a temperature profile having negative-positive-negative temperature gradients. Varying heat zones can be created or used to achieve those temperature gradients as shown in FIG. 12. For example, two heat zones can be used to create a single temperature gradient. In some embodiments, many heat zones (e.g., 5 or more) can be used to fine-tune temperature gradients.

In illustrative embodiments, a thermocouple 28 (or other temperature sensor) is secured to the heater support frame 22 between coils of the heating elements to measure the temperature. In some embodiments, thermocouple 28 can be positioned between coils of outlet heater assembly 18. The temperature at thermocouple 28 can be referred to as the outlet temperature of the compounds exiting the column 104 to the detector 106. The outlet terminating wires connect ends of the outlet heater assembly 18 to the heater controller circuit in the FCO controller 14.

In illustrative embodiments, a GC system 200 includes a high temperature valve 242 and a carrier gas bypass valve 246. Heat zones can include insulation barriers, such as a portion of insulation blanket, or other insulating material to limit heat transfer between zones. For example, an insulation barrier can be positioned between heat zone 6 and heat zone 7 to limit heat transfer between heat zone 6 and heat zone 7. In some embodiments, the heating capacity of heat zone 7 is less than the heating capacity of heat zones 4 and 5, and the heating capacity of heat zones 4 and 5 are less than the heading capacity of heat zone 6. Heat zone 7 is thermally separated from the other heat zones and does not form part of the positive temperature gradient. Heat zone 7 can be used to direct the effluent from the analytical column through a much lower temperature zone before going to the detector.

In illustrative embodiments, the analytical column 104 is wrapped or coiled around the column support frame 107 so that there is approximately equal spacing for each heat zone. The column support frame 107 can be a low mass open-hole metal screen in the shape of a cylinder. The low mass limits heat transfer, through the metal, from one heat zone to the next. The column support frame 107 can include ribs (not shown) to keep the column 104 in place directly over each heat zone. The ribs can be approximately equal distance from one another, so the coils of the column 104 can be counted in between each rib. For example, a 30 meter wide bore capillary column can have six coils wound between each 0.25" rib or divided substantially equally into approximately 4.25 meter sections. The diameter, or shape, of the column frame can be of various sizes to fit specific column types. For metal capillary columns, the diameter of the column support frame can be as small as, for example, 3.5 inches. A larger diameter support frame may be needed for wide bore fused silica capillary columns, which require a larger column coil to avoid stressing and breaking the column. The column support frame 107 can slide over the FCO 10, and the heater support frame 22 can be selected depending on the column type to fit. The column support frame 107 can contact the electrical insulation sheath 38 on one side and can be insulated on the column side, with insulation 109 for example, to seal the heat zone region of the FCO 10. The column 104 and heaters 16, 18 can be completely enveloped in insulation and protected from the outside environment. This provides technical utility and allows for operation in more exterior environments and temperatures than prior systems, in part because there is no fluid introduced inside the FCO 10 to cool the column 104 apart from natural diffusion to the surrounding environment.

In illustrative embodiments, the injector 102 is connected to the inlet portion 11 of the analytical column 104. In some embodiments, the distance between the injector 102 and the FCO 10 is minimized to mitigate the occurrence of cold spots. In addition, the FCO 10 can be equipped with heated transfer line tubing surrounding the analytical column 104. Separate transfer tubing can be connected to the inlet portion 11 and outlet portion 13 adjacent to heat zone 1 for the injector 102 and heat zone 6 for the detector 106 to transfer the heat thereto and mitigating cold spots between the FCO 10, the injector 102, and the detector 106 of the GC system 100. Any standard type of GC injector can be used to connect to the analytical column 104.

In illustrative embodiments, the primary column outlet 213 of the GC system 200 is connected to a high temperature valve 242. The high temperature valve 242 can be a low volume, three-way, high temperature valve or any other high temperature valve. In some embodiments a pressure switching device (e.g., a Deans switch) or other switching device can be used in place of the valve 242. Effluent from the analytical column passes through the selector valve 242 through the detector transfer line 245 (e.g., a short piece of column) to the detector 206 when the high temperature valve 242 is in the "OPEN" position. In this way, all of the tubing leading from the analytical column to the detector can be the same diameter.

In illustrative embodiments, any standard type of GC detector can be used with the FCO 10, 210; some examples are flame ionization detectors (FID), photoionization detectors (PID), helium ionization detectors (HID), thermal conductivity detectors (TCD), flame photometric detectors (FPD), nitrogen-phosphorus detectors (NPD), or a mass spectrometer (MS). A length of the transfer line 245 is minimized and can be routed along high temperature the heat zones of the FCO 210 and out through the insulation at any point that is convenient for a close connection to the detector 206. In some embodiments, the high temperature valve 242 and all connecting tubing are positioned next to the analytical column 104 in heat zone 2. In this way, these items are maintained at a higher temperature than the outlet temperature set-point to mitigate any cold spots.

In illustrative embodiments, effluent is directed to the secondary column 215 (e.g., a short piece of analytical column positioned in heat zone 7) when the selector valve 242 is in the "CLOSED" position. In some embodiments, the length of the secondary column 215 is equal to the length of column in each of the other heat zones to fit within heat zone 7 forming a secondary lower temperature path to the detector 206. In some embodiments, the secondary column 215 can contain a different stationary phase from the analytical column 204, or it can be a different diameter to enhance the separation ability. The secondary column 215 couples to the selector valve 242, where the effluent flows through the transfer line 245 to the detector 206. Heat zone 7 can be cooler such that the outlet set-point temperature provides two distinctly different outlet temperatures from the FCO 210 to the detector 206.

In illustrative embodiments, a length of the secondary column 215 can be adjusted longer, or shorter, depending on the lower temperature separation desired as long as the secondary column 215 is contained within heat zone 7. If a longer secondary column 215 is desired for the 2-dimensional analysis (e.g., 10, 15, or 30 meter) the size of heat zone 7 can be expanded to form a larger isothermal region to transfer the temperature profile to the secondary column 215. In some embodiments heat zone 7 is connected in series with the primary outlet heater 218 and the temperature of heat zone 7 follows accordingly with the set-point temperature for the primary outlet heater 218. The size of the FCO 210 would be expanded accordingly to accommodate the larger secondary column 215 and heat zone 7.

In illustrative embodiments, the temperature profile on the longer secondary column 215 (e.g., 10, 15, or 30 meter) could be controlled through a third independent 2D heater assembly 219 and 2D thermocouple 229 as shown in FIG. 16. The 2D heater assembly 219 can be formed from heating elements that are wrapped or coiled around the bottom of a heater support frame, for example below the primary outlet heater assembly 218. Similar to the inlet heater assembly 216 in construction and control, the 2D heater assembly 219 can form a single heat zone, or multiple heat zones, to control the temperature profile for the 2D heater assembly 219. A single heat zone would form an isothermal profile on that portion of the secondary column 215. Additional heating elements or varying heating elements can be used to create a plurality of heat zones of differing heating values. In some embodiments, there are three heat zones that are formed by heating elements attached end to end, which form the 2D heater assembly 219. The 2D heater assembly 219 is formed via resistance wires attached end to end for convenience. However, each heat zone could be separated into an individual heat zone (heater and thermocouple device) and could be controlled using separate temperature control circuits. Three heat zones are combined into one heating assembly for simplicity and ease of use in programming for the user, such as a GC analyst. In some embodiments, the heating capacity of earlier heat zones is greater than the heating capacity of later heat zones to form a negative temperature gradient for the 2D heater assembly 219. The size of the FCO 210 would be expanded accordingly to accommodate the larger secondary column 215 and 2D heater assembly 219.

In illustrative embodiments, with the high temperature valve 242 in the "OPEN" position, the carrier gas flows through the injector 202 into the analytical column 204. The carrier gas exiting the primary column outlet 213 of analytical column 204 flows through the high temperature valve 242 and then through the detector transfer line 245 to the detector 206. With the high temperature valve 242 in the "CLOSED" position, the carrier gas flows through the injector 202 into the analytical column 204, then the carrier gas exiting the primary column outlet 213 of analytical column 204 flows through the high temperature valve 242, which now diverts the effluent to the secondary column 215. The carrier gas exiting through the secondary column 215 passes again through the high temperature valve 242 and transfer line 245 to the detector 206. To allow enough time for the secondary column 215 to perform the separation, the carrier gas bypass valve 246 can be actuated to the closed position to stop the migration of sample material through the column 204 by directing the carrier gas to the secondary column 215. The carrier gas bypass valve 246 can be actuated by a solenoid, or any other actuation device used for switching a three-way valve.

In illustrative embodiments, both negative and positive temperature gradients can be used in the FCO 10. Through the injector 102, a sample of material enters the inlet portion 11 of the column 104. The inlet set-point temperature is programmed or determined to be high enough for all of the compounds in the material sample to elute as the sample travels down the negative gradient through heat zones 1-3. The inlet temperature can be measured in heat zone 1 to help ensure the inlet set-point temperature is accurate. With heat zone 1 used for the set-point temperature, heat zones 2 and 3 follow in a stable, predictable and linear fashion. For example, in some embodiments, if heat zone 1 is set to a high inlet temperature of 250° C., then heat zone 2 follows at 198° C. and heat zone 3 at 135° C. Heat zones 1-3 can be adjacent to one another, and can transfer some of the heat between them, forming a continuous gradient within the inlet heat zone region. Approximately the first half of the analytical column 104 is exposed to this negative gradient. In other embodiments, one or more of the heat zones can include insulating sheaths to decrease heat transfer between heat zones.

In illustrative embodiments, the second half of the analytical column 104 is positioned in heat zones 4-6 of the FCO 10, which can form a slightly positive temperature gradient. In other cases heat zones 4-6 could be equal or could form a secondary negative gradient. Typically, heat zone 6 is at a higher temperature than heat zones 4 and 5, and heat zone 6 is used for the outlet set-point temperature. In some embodiments, the same heater element is used for heat zones 1 and 6, while a second heater element is used for heat zones 2, 4, and 5, and a third heater element is used for heat zones 3 and 7. This provides the illustrative temperature gradients for operation and allows for standardization of parts and reduction of costs.

In illustrative embodiments, the inlet temperature is set to 250° C. and the outlet temperature is set to 150° C. The negative temperature gradient that starts in heat zone 1 is now extended through heat zone 5, which continues the peak focusing, sharpening, and separation started in heat zone 1 with the material sample introduction. As the compounds travel from heat zone 5 to heat zone 6, the material sample experiences a positive temperature gradient before entering the detector 106. This unique positive temperature gradient adds an additional level of sharpening to the peaks between heat zones 5 and 6. This extra squishing effect experienced by the peaks as they exit the analytical column is because the pressure inside the column in heat zone 6 is slightly higher than in heat zone 5.

In illustrative embodiments, the set-points of the inlet and outlet temperatures are variable and can be adjusted to suit the requirements for most GC methods. In some embodiments, the inlet temperature can be set to the final temperature of a conventional air bath temperature program, which will assure that the inlet is hot enough for all compounds to pass. The outlet temperature can determine which compounds, if any, are retained on the column. A lower temperature will retain more compounds, while a higher temperature will let more compounds pass through. Due to the negative gradient, the compounds eluting from the column are closer to their liquid phase temperature. Similar to traditional fluid ovens, if compounds condense on the column, they will not exit to the detector. Care must be taken to assure that the outlet temperature is high enough for the compounds to pass.

In illustrative embodiments, an additional heat zone 7 is used to analyze a broader range of compounds, along with a high temperature selector valve 242 (e.g., a low dead volume valve) and valve actuator, and carrier gas bypass valve 246 and actuator. The temperature of heat zone 7 can be set to be dependent on the outlet temperature set-point. In some embodiments, the outlet temperature set-point is 170° C., and the corresponding heat zone 7 temperature is 120° C. With two different selectable temperature heat zones for the compounds to travel, a broad range of analyses are possible.

In some embodiments an even broader range of 2D analysis is possible using a longer secondary column 215, a third independent 2D heater 219 (to create, for example, heat zones 7, 8 and 9) and control circuit, to create an expanded 2D heat zone (in place of the smaller heat zone 7) forming a gradient temperature profile on the secondary column 215. The range of analyses with either the single zone 7, or the expanded 2D heat zone is much broader than any known prior negative gradient systems.

In illustrative embodiments, the FCO 10 and column assembly 108 are packaged together, and can be installed in most commercially available GC systems by simply connecting inlet portion 11 to the provided injector, connecting outlet portion 13 to the provided detection system, and connecting FCO 10 to the provided controller. The carrier gas control, injector temperature, detector temperature, data collection and all other functions within the GC system would remain unchanged. The FCO can be used as the primary column oven, or two FCO's can be used in a dual oven configuration, allowing even small GC's such as the DPS Companion 2 to be used as a dual oven GC. The GC system can contain primary and secondary columns for a 2-dimensional analysis. The FCO can also be combined with a conventional air bath oven as the primary, or secondary column oven in a 2-dimensional analysis, or as a primary or secondary column oven to create a dual oven in a single oven GC.

The figures and descriptions provided herein may have been simplified to illustrate aspects that are relevant for a clear understanding of the herein described devices, systems, and methods, while eliminating, for the purpose of clarity, other aspects that may be found in typical devices, systems, and methods. Those of ordinary skill may recognize that other elements and/or operations may be desirable and/or necessary to implement the devices, systems, and methods described herein. Because such elements and operations are well known in the art, and because they do not facilitate a better understanding of the present disclosure, a discussion of such elements and operations may not be provided herein. However, the present disclosure is deemed to inherently include all such elements, variations, and modifications to the described aspects that would be known to those of ordinary skill in the art.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. Additionally, it should be appreciated that items included in a list in the form of "at least one of A, B, and C" can mean: (A); (B); (C); (A and B); (A and C); (B and C); or (A, B, and C). Similarly, items listed in the form of "at least one of A, B, or C" can mean: (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

While the disclosure has been illustrated and described in detail in the foregoing drawings and description, the same is to be considered as exemplary and not restrictive in character, it being understood that only illustrative embodiments thereof have been shown and described and that all changes and modifications that come within the spirit of the disclosure are desired to be protected.

The invention claimed is:

1. A system for performing gas chromatography analyses, the system comprising:
   an analytical column having an inlet portion coupled to an injector for receiving a material sample and an outlet portion coupled to a detector, the analytical column adapted to direct the material sample from the injector to the detector;
   an inlet heater coupled to the inlet portion of the analytical column and configured to produce one or more heat zones along the inlet portion of the analytical column;

an outlet heater coupled to the outlet portion of the analytical column and configured to produce one or more heat zones along the outlet portion of the analytical column; and
a controller operatively coupled to the inlet heater and the outlet heater,
wherein the controller is configured to selectively power the inlet heater and the outlet heater to define a steady-state temperature profile along the analytical column.

2. The system of claim 1, wherein the inlet heater is configured to produce at least a first heat zone along the inlet portion of the analytical column, wherein the outlet heater is configured to produce at least a second heat zone along the outlet portion of the analytical column.

3. The system of claim 2, wherein the first heat zone is maintained by the controller at a first temperature, the second heat zone is maintained by the controller at a second temperature, and wherein the first and second temperatures are different.

4. The system of claim 3, wherein the second temperature is less than the first temperature.

5. The system of claim 4, wherein at least one of the inlet heater and the outlet heater is configured to produce a third heat zone positioned between the first and second heat zones along the analytical column, wherein the third heat zone is maintained by the controller at a third temperature, and wherein the third temperature is less than both the first and second temperatures.

6. The system of claim 1, wherein at least a portion of the temperature profile has a negative temperature gradient.

7. The system of claim 6, wherein at least a portion of the temperature profile has a positive temperature gradient.

8. The system of claim 1, wherein at least a portion of the temperature profile has a positive temperature gradient.

9. The system of claim 1, further comprising an inlet temperature sensor coupled to the inlet heater and an outlet temperature sensor coupled to the outlet heater, and wherein the controller is configured to receive data from the inlet temperature sensor and the outlet temperature sensor.

10. A system for performing gas chromatography analyses, the system comprising:
an analytical column having an inlet portion coupled to an injector for receiving a material sample and an outlet portion coupled to a detector, the analytical column adapted to direct the material sample from the injector to the detector;
an inlet heater coupled to the inlet portion of the analytical column and configured to produce one or more heat zones along the inlet portion of the analytical column;
an outlet heater coupled to the outlet portion of the analytical column and configured to produce one or more heat zones along the outlet portion of the analytical column; and
a controller operatively coupled to the inlet heater and the outlet heater,
wherein the controller is configured to selectively power the inlet heater and the outlet heater to define a steady-state temperature profile along the analytical column, and the temperature profile has at least a first temperature gradient and a second temperature gradient.

11. The system of claim 10, wherein the first temperature gradient is negative and the second temperature gradient is positive.

12. The system of claim 11, wherein the first temperature gradient is defined by the inlet heater along the inlet portion of the analytical column and the second temperature gradient is defined by the outlet heater along the outlet portion of the analytical column.

13. A fluidless column oven for use in a gas chromatography system, the fluidless column oven comprising:
a support frame;
an inlet heater coupled to a first portion of the support frame; and
an outlet heater coupled to a second portion of the support frame different than the first portion,
wherein the inlet heater is configured to produce one or more heat zones and the outlet heater is configured to produce one or more heat zones, and the one or more heat zones produced by the inlet heater together with the one or more heat zones produced by the outlet heater define a steady-state temperature profile along the support frame.

14. The system of claim 13, wherein at least a portion of the temperature profile has a negative temperature gradient.

15. The system of claim 14, wherein at least a portion of the temperature profile has a positive temperature gradient.

16. The system of claim 13, wherein at least a portion of the temperature profile has a positive temperature gradient.

17. The system of claim 13, further comprising an inlet temperature sensor coupled to the support frame adjacent to the inlet heater and an outlet temperature sensor coupled to the support frame adjacent to the inlet heater adjacent to the outlet heater.

18. A system for performing gas chromatography analyses, the system comprising:
a column assembly including:
a column support frame; and
an analytical column coupled to the column support frame, the analytical column having an inlet portion coupled to an injector for receiving a material sample and an outlet portion coupled to a detector, the analytical column adapted to direct the material sample from the injector to the detector;
a fluidless column oven including:
a heater support frame;
an inlet heater coupled to the heater support frame adjacent to the inlet portion of the analytical column, the inlet heater configured to produce one or more heat zones along the inlet portion of the analytical column;
an outlet heater coupled to the heater support frame adjacent to the outlet portion of the analytical column, the outlet heater configured to produce one or more heat zones along the outlet portion of the analytical column; and
a controller operatively coupled to the inlet heater and the outlet heater,
wherein the fluidless column oven is configured to be received in the column assembly for heating of the analytical column, and the controller is configured to selectively power the inlet heater and the outlet heater to define a steady-state temperature profile along the analytical column.

* * * * *